US007438905B2

(12) United States Patent
Suzuki et al.

(10) Patent No.: US 7,438,905 B2
(45) Date of Patent: Oct. 21, 2008

(54) METHODS OF SUPPRESSING, TREATING, OR PREVENTING GRAFT REJECTION WITH AN ANTIBODY OR A PORTION THEREOF THAT BINDS TO AILIM

(75) Inventors: Seiichi Suzuki, deceased, late of Tokyo (JP); by Atsuko Suzuki, legal representative, Tokyo (JP); Mitsuaki Isobe, Tokyo (JP)

(73) Assignee: Japan Tobacco, Inc., Tokyo (JP)

( * ) Notice: Subject to any disclaimer, the term of this patent is extended or adjusted under 35 U.S.C. 154(b) by 597 days.

(21) Appl. No.: 10/793,171

(22) Filed: Mar. 4, 2004

(65) Prior Publication Data
US 2004/0253229 A1 Dec. 16, 2004

Related U.S. Application Data

(63) Continuation-in-part of application No. 10/451,972, filed as application No. PCT/JP02/00930 on Feb. 5, 2002, now abandoned.

(30) Foreign Application Priority Data

Mar. 1, 2001 (JP) ............................ 2001-56209
Mar. 1, 2001 (JP) ............................ 2001-56216
Jan. 16, 2002 (JP) ............................ 2002-8028

(51) Int. Cl.
*A61K 39/395* (2006.01)
*C07K 16/00* (2006.01)
*C07K 16/28* (2006.01)

(52) U.S. Cl. .............. 424/130.1; 424/133.1; 424/135.1; 424/141.1; 424/142.1; 424/154.1; 530/387.1; 530/388.1; 530/388.15; 530/388.22

(58) Field of Classification Search ........................ None
See application file for complete search history.

(56) References Cited

U.S. PATENT DOCUMENTS

| 5,484,892 A | 1/1996 | Tedder et al. |
| 5,506,126 A | 4/1996 | Seed et al. |
| 5,521,288 A | 5/1996 | Linsley et al. |
| 5,747,461 A | 5/1998 | Markov |
| 5,770,197 A | 6/1998 | Linsley et al. |
| 5,914,112 A | 6/1999 | Bedner et al. |
| 6,075,181 A | 6/2000 | Kucherlapati et al. |
| 6,531,505 B2 | 3/2003 | Xu et al. |
| 7,132,099 B2 * | 11/2006 | Kroczek ............... 424/130.1 |
| 2002/0115831 A1 | 8/2002 | Tamatani et al. |
| 2002/0164697 A1 | 11/2002 | Coyle et al. |
| 2002/0177191 A1 | 11/2002 | Kroczek |
| 2002/0182667 A1 | 12/2002 | Kroczek |
| 2004/0229790 A1 * | 11/2004 | Tezuka et al. ............... 514/12 |

FOREIGN PATENT DOCUMENTS

| AU | 752433 | 4/1999 |
| DE | 19821060 | 4/1999 |
| EP | 0 984 023 | 3/2000 |
| EP | 1 125 585 | 8/2001 |
| JP | 5-72204 | 3/1993 |
| JP | 11-228442 | 8/1999 |
| JP | 2000-154151 | 6/2000 |
| WO | WO 95/33770 | 12/1995 |
| WO | WO 97/26912 | 7/1997 |
| WO | WO 98/11909 | 3/1998 |
| WO | WO 98/19706 | 5/1998 |
| WO | WO 98/37415 | 8/1998 |
| WO | WO 98/38216 | 9/1998 |
| WO | WO 98/45331 | 10/1998 |
| WO | WO 99/15553 | 4/1999 |
| WO | WO 00/19988 | 4/2000 |
| WO | WO 00/46240 | 8/2000 |
| WO | WO 00/67788 | 11/2000 |
| WO | WO 01/08700 | 2/2001 |
| WO | WO 01/12658 | 2/2001 |
| WO | WO 01/15732 | 3/2001 |
| WO | WO 01/18022 | 3/2001 |
| WO | WO 01/21796 | 3/2001 |
| WO | WO 01/32675 | 5/2001 |
| WO | WO 02/44364 | 6/2001 |
| WO | WO 01/64704 | 9/2001 |
| WO | WO 01/87981 | 11/2001 |
| WO | WO 02/70010 | 9/2002 |
| WO | WO 02/76504 | 10/2002 |

OTHER PUBLICATIONS

Huang, Pharmacology and Therapeutics, 2000, 86:201-215.*
English translation of WO 02/070010.*
The Merck Manual of Diagnosis and Therapy (Merck Research Laboratories, 1999, 17th Edition, pp. 1072-1073).*
Waldmann et al., Phil. Trans. R. Soc. Lond. B 2001, vol. 356, pp. 659-663.*
Samstein et al., Phil. Trans. R. Soc. Lond. B 2001, vol. 356, pp. 749-758.*
Calne R., Phil. Trans. R. Soc. Lond. B 2001, vol. 356, pp. 767-771.*
Dai et al., (1999) "The role of cytokines, CTLA-4 and costimulation in transplant tolerance and rejection," Current Opinion in Immunology, vol. 11, No. 5, pp. 504-508.
Nanji et al., (2003) "Combination Therapy With Anti-ICOS and Cyclosporine Enhances Cardiac but Not Islet Allograft Survival," Transplantation Proceedings, vol. 35, No. 7, pp. 2477-2478.
Abbas, "T-cell stimulation: an abundance of B7s," Nat Med. 5(12):1345-6 (1999).
Abrams et al., "CTLA4Ig-mediated blockage of T-cell constimulation in patients with psoriasis vulgaris," J. Of Clin. Invest. 103(9):1243-1252 (1999).

(Continued)

*Primary Examiner*—Ilia Ouspenski
(74) *Attorney, Agent, or Firm*—Fish & Richardson P.C.

(57) ABSTRACT

Graft rejection is a serious problem associated with tissue or organ transplantation (e.g., allotransplantation or xenotransplantation), performed to treat various organ failures (e.g., liver, heart, lung, kidney, or pancreas). Described are pharmaceutical compositions for suppressing, treating, or preventing graft rejection comprising a substance having an activity to modulate signal transduction mediated by AILIM, and a pharmaceutically acceptable carrier.

26 Claims, 5 Drawing Sheets

OTHER PUBLICATIONS

Aicher et al., "Characterization of human inducible costimulator ligand expression and function," J. Of Immunology 164:4689-4696 (2000).

Akbari et al., "Antigen-specific regulatory T cells develop via the ICOS-ICOS-ligand pathway and inhibit allergen-induced airway hyperreactivity," Nature Medicine 8(9):1024-1032 (2002).

Andersen et al., "Allelic variation of the inducible costimulator (ICOS) gene: detection of polymorphisms, analysis of the promoter region, and extended haplotype estimation," Tissue Antigens 61: 276-285 (2003).

Ara et al., "Potent activity of soluble B7RP-1-FC in therapy of murine tumors in syngeneic hosts," Int. J. Cancer 103:501-507 (2003).

Arimura et al., "A co-stimulatory molecule on activated T cells, H4/ICOS, delivers specific signals in $T_h$ cells and regulates their responses," International Immunology 14(6):555-566 (2002).

Bojarth, "A molecular model of inducible costimulator protein and three-dimensional analysis of its relation to the CD28 family of T cell-specific costimulatory receptors," J. Mol. Model 5:169-176 (1999).

Beier et al., "Induction, binding specificity and function of human ICOS," Eur. J. Immunol. 30:3707-3717 (2000).

Bennett et al., "Program death-1 engagement upon TCR activation has distinct effects on costiumulation and cytokine-driven proliferation: Attenuation of ICOS, IL-4, and IL-21, but not CD28, IL-7, and IL-15 responses" J. of Immunol. 170:711-718 (2003).

Bensimon et al., "Human lupus anti-DNA autoantibodies undergo essentially primary V kappa gene rearrangements," Embo J. 13(13):2951-62 (1994).

Bertram et al., "Role of ICOS versus CD28 in antiviral immunity," Eur. J. Immunol. 32:3376-3385 (2002).

Biacone et al., "Lymphocyte costimulatory receptors in renal disease and transplantation," J. Nephrol 15:7-16 (2002).

Blazar et al., "CD4+ cells tolerized ex vivo to host alloantigen by anti-CD40 ligand . . . antigen response," J. Clin. Invest. 102(3):473-482 (1998).

Blazar et al., "Coblockade of the LFA1:ICAM and CD28/CTLA4:B7 pathways is a highly . . . donor grafts," Blood 85(9):2607-2618 (1995).

Bonhagen et al., "ICOS+ Th Cells produce distinct cytokines in different mucosal immune responses," Eur. J. Immunol. 33:392-401 (2003).

Brodie et al., "LICOS, a primordial costimulatory ligand?" Current Biology 10(6):333-336 (2000).

Buonfiglio et al., "Characterization of a novel human surface molecule selectively expressed by mature thymocytes, activated T cells and subsets of T cell lymphomas," Eur. J. Immunol. 29:2863-2874 (1999).

Buonfiglio et al., "The T cell activation molecule H4 and the CD28-like molecule ICOS are identical," Eur. J. Immunol. 30:3463-3467 (2000).

Cameron "Recent advances in transgenic technology" Molecular Biotechnology 7:253-65 (1997).

Campbell et al., "Separable effector T cell populations specialized for B cell help or tissue inflammation," Nat Immunol. 2(9):876-81 (2001).

Carreno et al., "The B7 family of ligands and its receptors," Annu. Rev. Immunol. 20:29-53 (2000).

Chambers, "The expanding world of co-stimulation: the two-signal model revisted," Trends in Immunology 22(4):217-223 (2001).

Chapoval et al., "B7-H3: a constimulatory molecule for T cell activation and IFN-gamma production," Nat Immunol. 2(3):269-74 (2001).

Cocks et al., "A novel receptor involved in T-cell activation," Nature, 376:260-263 (1995).

Coyle et al., "The CD28-related molecule ICOS is required for effective T cell-dependent immune responses," Immunity 13:95-105 (2000).

Deng et al., "Critical role of CD81 in cognate T-B cell interactions leading to $T^h2$ responses," International Immunology 14(5):513-523 (2002).

Dong et al., "B7-H1, a third member of the B7 family, co-stimulates T-cell proliferation and interleukin-10 secretion," Nat. Med. 5(12):1365-9 (1999).

Dong et al., "Cutting Edge: Critical role of inducible costimulator in germinal center reactions" The J. Immunol. 166:3659-3662 (2001).

Dong et al., "ICOS co-stimulatory receptor is essential for T-cell activation and function," Nature 409:97-101 (2001).

Eljaschewitsch et al., "Identification of a novel activation antigen on human CD4+ T cells," Immunobiol., 194(1-3):27 (1995).

Feito et al., "Mechanisms of H4/ICOS costimulation: effects on proximal TCR signals and MAP kinase pathways," Eur. J. Immunol. 33:204-214 (2003).

Flesch, "Inducible costimulator (ICOS)," J. of Biol. Regul.Homeost. Agents 16:214-216 (2002).

Flesch, "Inducible costimulator-ligand (ICOS-L)," J. of Biol. Regul. Homeost. Agents 16:217-219 (2002).

Frauwirth et al., "Activation and inhibition of lymphocytes by costimulation," J. of Clin. Invest. 109(3):295-299 (2002).

Fijisawa et al., "Presence of high contents of thymus and activation-regulated . . . dermatitis," J. Allergy of Clin. Immunol. 110(1):139-146 (2002).

Goding, "Monoclonal Antibodies: Principles and Practive," 2nd Edition, Academic Press, Orlando, Florida, Chapter 8, pp. 281-293 (1986).

Goni et al., "Structural and idiotypic characterization of the L chains of human IgM autoantibodies with different specificities," J. Immunol. 142(9):3158-63 (1989).

Gonzalo et al., "Cutting edge: The related molecules CD28 inducible costimulator deliver both unique and complementary signals required for optimal T cell activation," J. of Immunol. 166:1-5 (2001).

Gonzalo et al., "ICOS is critical for T helper cell-mediated lung mucosal inflammatory responses," Nat Immunol. 2(7):597-604 (2001).

Greenwald et al., "Cutting edge: Inducible costimulator protein regulates both Th1 and Th2 responses to cutaneous leishmaniasis," J. of Immunol. 168:991-995 (2002).

Greenwald et al., "Negative co-receptors on lymphocytes," Current Opinion in Immunology 14:391-396 (2002).

Grimbacher et al., "Homozygoud loss of ICOS is associated with adult-onset common variable immunodeficiency," Nature Immunology 4(3):261-268 (2003).

Guinan et al., "Transplantation of anergic histoincompatible bone marrow allografts," The New England J. of Med. 340:1704-1714 (1999).

Guo et al., "Stimualtory effects of B7-related protein-1 on cellular and humoral immune response in mice," J. of Immunol. 166:5578-5584 (2001).

Guo et al., "Prolonged survival in rat liver transplanatation with mouse monoclonal antibody against an inducible costimulator (ICOS)," Transplantation 73(7):1027-1032 (2002).

Haimila et al., "Genetic polymorphism of the human ICOS gene," Immunogenetics 53:1028-1032 (2002).

Hanzawa et al., "Characteristics of a TTH1 antibody which blocks an unknown adhesion pehnomenon," Proceedings of the Japanese Society for Immunology, vol. 24, Abstract No. W17-13 (1994) [Original Japanese and English Language Translation].

Harada et al., "A single amino acid alteration in cytoplasmic domain determines IL-2 promoter activation by ligation of CD28 but not inducible costimulator (ICOS)," J. Exp. Med. 197(2):257-262 (2003).

Harlow and Lane, "Antibodies: A Laboratory Manual," Cold Spring Harbor Laboratory, p. 285 (1988).

Heyeck et al., "Developmental regulation of a murine T-cell-specific tyrosine kinase gene, Tsk," Proc. Natl. Acad. Sci. USA, 90:669-673 (1993).

Houdebine "Production of pharmaceutical proteins from transgenic animals" J. Biotechnol. 34:269-87 (1994).

Hutloff et al., "ICOS is an inducible T-cell co-stimulator structurally and functionally related to CD28," Nature 397:263-266 (1999).

Hutloff et al., "Identification and inital characterization of a novel T cell-specific cell surface activation antigen," Immunobiol., 197(2-4):172 (1997).

Ihara et al., "Association studies of CTLA-4, CD28, and ICOS gene polymorphisms with type 1 diabetes in the Japanese population," Immunogenetics 53(6):447-54 (2001).

Iiyama et al., "The role of inducible co-stimulator (ICOS)/B7-related protein-1 (B7RP-1) interaction in the functional development of Peyer's patches," Immunology Letters, In Press, Uncorrected Proof available online Apr. 11, 2003, http://www.sciencedirect.com/science/journal/01652478.

Ishikawa et al., "Prediction of the Coding Sequences of Unidentified Human Genes. X. The Complete Sequences of 100 New cDNA Clones from Brain Which Can Code for Large Proteins in vitro," DNA Research, 5:169-176 (1998).

Iwai et al., "Amelioration of collagen-induced arthritis by blockade of inducible costimulator-B7 homologous protein costimulation," J. Of Immunol. 169:4332-4339 (2002).

Kappel et al. "Regulating gene expression in transgenic animals" Current Opinion in Biotechnology 3:548-53 (1992).

Kanai et al., "ICOS costimulation in inflammatory bowel disease," J. Of Gastroenterology 37(14):78-81 (2002).

Khayyamian et al., "ICOS-ligand, expressed on human endothelial cells, costimulates Th1 and Th2 cytokine secretion by memory CD4$^+$ T cells," PNAS 99(9):6198-6203 (2002).

Kirchhofer et al., "Role of collagen-adherent platelets in mediating fibrin formation in flowing whole blood," Blood 86(10):3815-3822 (1995).

Kopf et al., "Inducible costimulator protein (ICOS) controls T helper cell subset polarization after virus and parasite infection," J. Exp. Med. 192(1):53-61 (2000).

Kosuge et al., "Induction of immunologic tolerance to cardiac allograft by simultaneous blockade of inducible co-stimulator and cytotoxic T-lymphocyte antigen 4 pathway," Transplantation 75(8):1374-1379 (2003).

Kuchroo et al., "B7-1 and B7-2 costimulatory molecules activate differentially the Th1/Th2 developmental pathways: Application to autoimmune disease therapy," Cell, 80:707-718 (1995).

Lamhemedi-Cherradi et al., "Further mapping of the Idd5.1 locus for autoimmune diabetes in NOD mice," Diabetes 50(12):2874-8 (2001).

Liang et al., "Constitutive expression of the B7h ligand for inducible constimulator . . . CD40 signalling," J. Exp. Med. 196(1):97-108 (2002).

Lin et al., "Long-term acceptance of major histocompatibility complex mismatched cardiac allografts induced by CTLA4Ig plus donor-specific transfusion," J. Exp. Med. 178:1801-1806 (1993).

Ling et al., "Assembly and annotation of human chromosome 2q33 sequence containing the CD28, CTLA4, and ICOS gene cluster: analysis by computational, comparative, and microarray approaches," Genomics 78(3):155-68 (2001).

Ling et al., "Cutting edge: Identification of GL50, a novel B7-like protein that functionally binds to ICOS receptors," J. of Immunol. 164:1653-1657 (2000).

Ling et al., "Differential expression of inducible costimulator-ligand splice variants: lymphoid regulation of mouse GL50-B and human GL50 molecules," J Immunol. 166(12):7300-8 (2001).

Linsley, "T cell activation: you can't get good help," Nat Immunol. 2(2):139-40 (2001).

Liu et al. "B7H costimulates clonal expansion of, and cognate destruction of tumor cells by, CD8(+) T lymphocytes in vivo," J Exp Med. 194(9):1339-48 (2001).

Lucia et al., "Expression of the novel T cell activation molecule hpH4 in HIV-infected patients: Correlation with disease status", AIDS Research and Human Retroviruses 16(6):549-557 (2000).

Löhning et al., "Expression of ICOS in vivo defines CD4$^+$ effector T cells with high inflammatory potential and a strong bias for secretion of interleukin 10," J. Exp. Med. 197(2):181-193 (2003).

Mackay et al., "Follicular homing T helper (Th) cells and the Th1/Th2 paradigm," J Exp Med. 192(11):F31-4 (2000).

Mages et al., "Molecular cloning and characterization of murine ICOS and identification of B7h as ICOS ligand," Eur. J. Immunol. 30:1040-1047 (2000).

Marguet et al., "cDNA Cloning for Mouse Thymocyte-activating Molecule," The Journal of Biological Chemistry, 267(4):2200-2208 (1992).

Matsui et al., "Adenovirus-mediated gene transfer of ICOSIg fusion protein ameliorates ongoing experimental autoimmune myocarditis," Human Gene Therapy 14:521-532 (2003).

McAdam et al., "ICOS is critical for CD40-mediated antibody class switching," Nature 409:102-104 (2001).

McAdam et al., "Mouse inducible costimulatory molecule (ICOS) expression is enhanced by CD28 costimulation and regulates differentiation of CD$^+$ T cells," J. of Immunol. 165:5035-5040 (2000).

McAdam et al. (2000) "Mouse inducible costimulatory (ICOS) molecule expression is increased by CD28 costimulation and regulates development of Th2 cells," FASEB Journal, 14(6):A1169.

Mittrücker et al., "Inducible costimulator protein controls the protective T cell response against *Listeria monocytogenes*," J. of Immunol. 169:5813-5817 (2002).

Mullins et al. "Expression of the DBA/2J Ren-2 gene in the adrenal gland of transgenic mice" EMBO J., 8:4065-72 (1989).

Mullins et al. "Fulminant hypertension in transgenic rats harbouring the mouse Ren-2 gene" Nature, 344:541-44 (1990).

Mullins et al. "Transgenesis in nonmurine species" Hypertension 22:630-33 (1993).

Mueller et al., "T cells: A proliferation of costimulatory molecules," Current Biol. 10(6):227-230 (2000).

Nakamura et al., "Acceptance of islet allografts in the liver of mice by blockade of an inducible costimulator," Transplantation 75(8):1115-1118 (2003).

Niemann "Transgenic farm animals get off the ground" Transgenic Research, 7:73-75 (1998).

Nojima et al., "The 4F9 antigen is a member of the tetra spans transmembrane protein family and functions as an accessory molecule in T cell activation and adhesion," Cellular Immunology, 152:249-260 (1993).

Nurieva et al., "Inducible costimulator is essential for collagen-induced arthritis," J. Clin. Invest. 111(5):701-06 (2003).

Ogasawara et al., "Inducible costimulator costimulates cytotoxic activity and IFN-γ production in activated murine NK cells," J. of Immunol. 169:3676-3685 (2002).

Ogawa et al., "Opposing effects of anti-activation-inducible lymphocyte-immunomodulatory molecule/inducible costimulator antibody on the development of acute versus chronic graft-versus-host disease," J Immunol. 167(10):5741-8 (2001).

Okamoto et al., "Expression and function of the co-stimulator H4/ICOS on activated T cells of patients with rheumatoid arthritis," J. of Rheumatology 30:1157-1163 (2003).

Okazaki et al., "New regulatory co-receptors: inducible co-stimulator and PD-1," Current Opinion on Immunology 14:779-782 (2002).

Overbeek "Factors affecting transgenic animal production," Transgenic Animal Technology, A Laboratory Handbook 96-98 (1994).

Ozkaynak et al., "Importance of ICOS-B7RP-1 costimulation in acute and chronic allograft rejection," Nature Immunology 2(7):591-596 (2001).

O'Neill, "Co-stimulating allergy," Trends Immunol. 22(4):183 (2001).

Parry et al., "CD28 and inducible costimulatory protein Src homology 2 binding domains show distinct regulation of phosphatidylinositol 3-kinase, Bcl-$x_L$, and IL-2 expression in primary human CD4 T lymphocytes," J. of Immunol. 171:166-174 (2003).

Pech et al., "A large section of the gene locus encoding human immunoglobulin variable regions of the kappa type is duplicated," J. Mol Biol. 183(3):291-9 (1985).

Poster, Kyoto International Conference Hall, Takaragaike Sakyo-ku, Kyoto, Japan (Nov. 30, 1994) [Original Japanese and English Language Translation].

Pound, "A new T-helper cell subset?" Trends Immunol. 22(4):182-3 (2001).

Redoglia et al., "Characterization of H4: a mouse T lymphocyte activation molecule functionally associated with CD3/T cell receptor," Eur. J. Immunol. 26:2781-2789 (1996).

Reiser et al., "Costimulatory B7 molecules in the pathogenesis of infectious and autoimmune diseases," The New England J. of Med. 335(18):1369-1377 (2003).

Richter et al., "Tumor necrosis factor-α regulates the epxpression of inducible costimulator receptor ligand on CD34+ progenitor cells during differentiation into antigen presenting cells," J. of Biological Chem. 276(49):45686-45693 (2001).

Riley et al., "ICOS Costimulation requires IL-2 and can be prevented by CTLA-4 engagement," J. Immunol. 166:4943-4948 (2001).

Riley et al., "Modulation of TCR-induced transcriptional profiles by ligation of CD28, ICOS, and CTLA-4 receptors," PNAS 99(18):11790-11795 (2002).

Robert et al., "Antibody Cross-Linking of the Thymocyte-Specific Cell Surface Molecule CTX Causes Abnormal Mitosis and Multinucleation of Tumor Cells," Experimental Cell Research, 235:227-237 (1997).

Rottman et al., "The costimulatory molecule ICOS plays an important role in the immunopathogenesis of EAE," Nat Immunol. 2(7):605-11 (2001).

Rutitzky et al., "Disruption of the ICOS-B7RP-1 costimulatory pathway leads to enhanced hepatic immunopathology and increased gamma interferon production by CD4 T cells in murine schistosomiasis," Infection and Immunity 71(7):4040-4044 (2003).

Sakamoto, "Mabs against human, rat, and mouse AILIM/ICOS," Hybridoma and Hybridomics 21(1):86-87 (2002).

Sakamoto et al., "AILIM/ICOS: its expression and functional analysis with monoclonal antibodies," Hybridoma and Hybridomics, 20(5):293-303 (2001).

Salama et al., "Interaction between ICOS-B7RPI and B7-CD28 costimulatory pathways in alloimmune responses *in vivo*," American J. of Transplantation 3:390-395 (2003).

Sato et al., "Up-regulation of inducible co-stimulator (ICOS) expression and its regulation of cytokine production in inflammatory bowel disease," Gastroenterology 118(4):A662.

Sayegh, "Finally, CTLA4Ig graduates to the clinic," J. of Clin. Invest. 103(9):1223-1225 (1999).

Schwartz, "Immunology. It takes more than two to tango," Nature 409(6816):31-2 (2001).

Sharpe et al., "The B7-CD28 superfamily," Nature Reviews Immunology 2:116-126 (2002).

Sharpe, "Analysis of lymphocyte costimulation *in vivo* using transgenic and 'knockout' mice," Current Opinion in Immunology, 7:387-395 (1995).

Sigmund "Are studies in genetically altered mice out of control?" Arterioscler. Thromb. Vasc. Biol., 20:1425-29 (2000).

Smith et al., "Inducible constimulatory molecule-B7-related protein 1 interactions are important for the clonal expansion and B cell helper functions of naïve, Th1, and Th2 T cells," J. of Immunol. 170:2310-2315 (2003).

Sperling et al., "ICOS costimulation: It's not just for TH2 cells anymore," Nat Immunol. 2(7):573-4 (2001).

Sperling, "ICOS costimulation: is it the key to selective immunotherapy?," Clin Immunol. 100(3):261-2 (2001).

Sporici et al., "ICOS ligand costimulation is required for T-cell encephalitogenicity," Clin Immunol. 100(3):277-88 (2001).

Sporici et al., "Costimulation of memory T-cells by ICOS: a potential therapeutic target for autoimmunity?" Clin Immunol. 100(3):263-9 (2001).

Storb et al., "Stable mixed hematopoietic chimerism in dogs given donor antigen, CTLA4Ig, and 100 cGy total body irradiation before . . . marrow transplant," Blood 94(7):2523-2529 (1999).

Stuart et al., "Targeting T cell costimulation in autoimmune disease," Expert Opin. Ther. Targets 6(3):275-289 (2002).

Swallow et al., "B7h, a novel costimulatory homolog of B7.1 and B7.2, is induced by TNFα," Immunity 11:423-432 (1999).

Tafuri et al., "ICOS essential for effective T-helper-cell responses," Nature 409:105-109 (2001).

Tai et al., "A role for CD9 molecules in T cell activation," J. Exp. Med., 184:753-758 (1996).

Tamatani et al., "AILIM/ICOS: a novel lymphocyte adhesion molecule," Intl. Immunol. 12(1):51-55 (2000).

Tamatani et al., "Characteristics of an antibody which induces an ICAM-I-LFA-l-independent adhesion pathway," Proceedings of the Japanese Society for Immunology, vol. 23, Abstract No. H-160 (1993) [Original Japanese and English Language Translation].

Tamura et al., "B7-H1 costimulation preferentially enhances CD28-independent T-helper cell function," Blood 97(6):1809-16 (2001).

Tesciuba et al., "Inducible costimulator regulates Th2-mediated inflammation, but not Th2 differentiation, in a model of allergic airway disease," J Immunol. 167(4):1996-2003 (2001).

Tezuka et al., "Identification and characterization of rat AILIM/ICOS, a novel T-cell costimulatory molecule, related to the CD28/CTLA4 family," Biochem. & Biophysical Res. Comm. 276:335-345 (2000).

Tezuka et al., "Genetic cloning of a lymphocyte surface signal transduction molecule which induces an unknown adhesion phenomenon," Proceedings of the Japanese Society for Immunology, vol. 24, Abstract No. W17-14 (1994) [Original Japanese and English Language Translation].

Tomlinson et al., "The repertoire of human germline VH sequences about fifty groups of VH segments with different hypervariable loops," J. Mol. Biol. 227(3):776-98 (1992).

Totsuka et al., "Ameliorating effect of anti-inducible costimulator monoclonal antibody in a murine model of chronic colitis," Gastroenterology 124:410-421 (2003).

Vermaelen et al., "Accelerated airway dendritic cell maturation, trafficking and elimination in a mouse model of asthma," Am J Respir Cell Mol Biol. 29(3 Pt 1):405-9 (2003).

Villegas et al., "A role for inducible costimulator protein in the CD28-independent mechanism of resistance to *toxoplasma gondii*," J. of Immunol. 169:937-943 (2002).

Wahl et al., "Renal tubular epithelial expression of the costimulatory molecule B7RP-1 (Inducible Costimulator Ligand)," J. Am. Soc. Nephrol. 13:1517-1526 (2002).

Wall "Transgenic livestock: progress and prospects for the future" Theriogenology 45:57-68 (1996).

Wallin et al., "Enhancement of CD8+ T cell responses by ICOS/B7h costimulation," J Immunol. 167(1):132-9 (2001).

Wang et al., "Costimulation of T cells by B7-H2, a B7-like molecule that binds ICOS," Blood 96(8):2808-2813 (2000).

Wang et al., "Ligand binding sites of inducible costimulator and high avidity mutants with improved function," J. Exp. Med. 195(8):1033-1041 (2002).

Wekerle et al., "Allogeneic bone marrow transplantation with costimulatory blockade induces macrochimerism and tolerance without cytoreductive host treatment," Nature Medicine 6(4):464-469 (2000).

Wiendl et al., "Muscle fibres and cultured muscle cells express the B7.1/2-related inducible co-stimulatory molecule, ICOSL: implications for the pathogenesis of inflammatory myopathies," Brain 126:1026-1035 (2003).

Wiley et al., "Evaluation of inducible costimulator/B7-related protein-1 as a therapeutic target in a murine model of allergic airway inflammation," Am. J. Respir. Cell Mol. Biol. 28:722-730 (2003).

Witsch et al., "ICOS and CD28 reversely regulate IL-10 on re-activation of human effector T cells with mature dendritic cells," Eur. J. Immunol. 32:2680-2686 (2002).

Wong et al., "Impaired germinal center formation and recall T cell-dependent immune responses in mice lacking the co-stimulatory ligand B7-H2," Blood 102(4):1381-1388 (2003).

Yoshinaga et al., "Characterization of a new human B7-related protein: B7RP-1 is the ligand to the co-stimulatory protein ICOS," International Immunol. 12(10):1439-1447 (2000).

Yoshinaga et al., "T-cell co-stimulation through B7RP-1 and ICOS," Nature 402:827-832 (1999).

* cited by examiner

| TREATMENT | NUMBER OF ANIMALS | DURATION OF GRAFT SURVIVAL OF THE TRANSPLANTED LIVER (DAYS) | AVERAGE (DAYS) | TEST VALUE (P$^a$) |
|---|---|---|---|---|
| CONTROL | 6 | 10, 11, 11, 11, 12, 12 | 11.1 | |
| ANTI-AILIM ANTIBODY (1mg/kg; IV INJECTION; DAY 0) | 5 | 10, 10, 11, 12, 13 | 11.2 | |
| ANTI-AILIM ANTIBODY (1mg/kg; IV INJECTION; DAY 0 AND 6) | 5 | 10, 11, 11, 12, 14 | 11.6 | |
| ANTI-AILIM ANTIBODY (1mg/kg; IV INJECTION; DAY 0, 3, AND 6) | 7 | 10, 14, 16, 25, 28, 30*, 30* | >21.9 | <0.001 |
| ANTI-AILIM ANTIBODY (1mg/kg; IV INJECTION; DAY 0, 3, 6, 9, AND 12) | 9 | 13, 16, 19, 19, 23, 25, 29, 31, 32 | 23 | <0.001 |
| ANTI-AILIM ANTIBODY (0.3mg/kg; IV INJECTION; DAY 0, 3, 6, 9, AND 12) | 6 | 12, 12, 14, 17, 25, 27 | 17.8 | <0.001 |
| FK-506 (1mg/kg; IM INJECTION; DAY 0) | 8 | 22, 24, 26, 30, 30*, 30*, 19*, 19* | 15.5 | |
| ANTI-AILIM ANTIBODY (1mg/kg; IV INJECTION; DAY 0) AND FK-506 (1mg/kg; IM INJECTION; DAY 0) | 8 | 17, 41, 47, 56, 19*, 19*, 64*, 129* | >49.0 | <0.001 | a: WHEN COMPARED TO THE CONTROL GROUP
*: GRAFT STILL SURVIVING

FIG. 1

| TREATMENT | NUMBER OF ANIMALS | DURATION OF GRAFT SURVIVAL OF TRANSPLANTED LIVER (DAYS) | INTERMEDIATE VALUE (DAYS) | TEST VALUE (Pa) |
|---|---|---|---|---|
| CONTROL (UNTREATED) | 6 | 10, 11, 11, 11, 12, 12 | 11 | |
| ANTI-AILIM ANTIBODY (1mg/kg; IV INJECTION; DAY 0, 3, 6, 9, AND 12) | 9 | 13, 16, 19, 19, 23, 25, 29, 31, 32 | 23 | <0.001 |
| FK-506 (1mg/kg; IM INJECTION; DAY 0) | 8 | 19, 22, 24, 26, 30, 42, 45, 91 | 28 | <0.001 |
| ANTI-AILIM ANTIBODY (1mg/kg; IV INJECTION; DAY 0) AND FK-506 (1mg/kg; IM INJECTION; DAY 0) | 9 | 17, 35, 38, 41, 47, 56, 58, >100, >100 | >44 | <0.001 |
| ANTI-AILIM ANTIBODY (1mg/kg; IV INJECTION; DAY 0, 3, AND 6) AND FK-506 (1mg/kg; IM INJECTION; DAY 0) | 2 | 45, 69 | 57 | |

FIG. 2

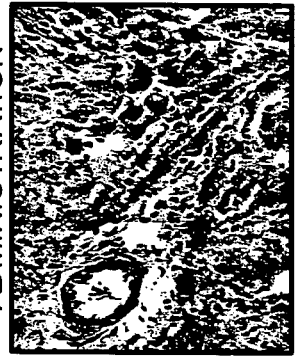
UNTREATED GROUP
X200
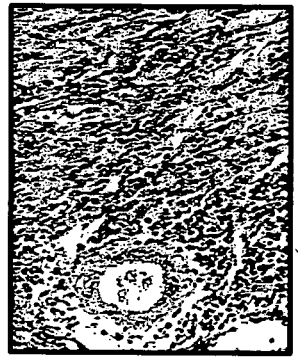
ICOS ANTIBODY ADMINISTRATION
X200
FIG. 4
| TREATMENT | NUMBER OF ANIMALS | SKIN TRANSPLANTATION (PRIMARY) | | HEART TRANSPLANTATION (SECONDARY) | | HEART TRANSPLANTATION (PRIMARY) | |
|---|---|---|---|---|---|---|---|
| | | REJECTION | GRAFT SURVIVAL | REJECTION | GRAFT SURVIVAL | REJECTION | GRAFT SURVIVAL |
| ALLOTRANSPLANTATION/ AdCTLA4-Ig | 2 | 2/2 | 0/2 | | | 2/2 | 0/2 |
| ALLOTRANSPLANTATION/ AdCTLA4-Ig+ANTI-AILIM ANTIBODY | 5 | 2/2 | 0/2 | 0/3 | 3/3 | 0/5 | 5/5 |
FIG. 6

| TREATMENT | NUMBER OF ANIMALS | DURATION OF GRAFT SURVIVAL OF THE TRANSPLANTED HEART (DAYS) | INTERMEDIATE VALUE (DAYS) | TEST VALUE (P) |
|---|---|---|---|---|
| CONTROL (UNTREATED) | 10 | 5, 5, 5, 6, 6, 6, 6, 6, 6, 6 | 6 | |
| ISOTRANSPLANTATION/UNTREATED | 4 | >250, >250, >250, >250 | >250 | |
| ALLOTRANSPLANTATION/AdLacZ | 7 | 6, 6, 6, 6, 7, 7, 7 | 6 | |
| ALLOTRANSPLANTATION/AdCTLA4-Ig | 10 | 40, 42, 58, 62, 64, 65, 68, 109, 140[a], 140[a] | 64 | <0.001 |
| ALLOTRANSPLANTATION/ANTI-AILIM ANTIBODY | 7 | 5, 5, 6, 6, 6, 6, 6 | 6 | |
| ALLOTRANSPLANTATION/AdCTLA4-Ig + ANTI-AILIM ANTIBODY | 5 | >250[b], >250[b], >250[b], >250[a], >250[a] | >250 | <0.001 | a: PRIMARY SKIN TRANSPLANTATION
b: SECONDARY HEART TRANSPLANTATION

FIG. 5

METHODS OF SUPPRESSING, TREATING, OR PREVENTING GRAFT REJECTION WITH AN ANTIBODY OR A PORTION THEREOF THAT BINDS TO AILIM

CROSS REFERENCE TO RELATED APPLICATIONS

This application is a continuation-in-part of U.S. application Ser. No. 10/451,972, filed Jun. 27, 2003, now abandoned which is a U.S. national phase of International Application No. PCT/JP02/00930, filed Feb. 5, 2002, which claims priority from Japanese Application No. 2001-56209, filed Mar. 1, 2001, Japanese Application No. 2001-56216, filed Mar. 1, 2001, and Japanese Application No. 2002-8028, filed Jan. 16, 2002. The prior applications are incorporated herein by reference in their entirety.

TECHNICAL FIELD

The present invention relates to pharmaceutical compositions comprising a substance having an activity to modulate the biological activity of the "activation inducible lymphocyte immunomodulatory molecule" (AILIM) (also known as "inducible costimulator" (ICOS)), especially the signal transduction mediated by AILIM.

Specifically, the present invention relates to pharmaceutical compositions comprising a substance having an activity to modulate (for example, inhibit) the proliferation of AILIM-expressing cells or modulate (for example, inhibit) the production of a cytokine (for example, interferon-γ, or interleukin-4) by AILIM-expressing cells.

More specifically, the present invention relates to (1) pharmaceutical compositions for inhibition, treatment, or prevention of graft rejection (immunological rejection) accompanying the transplantation of an organ, a portion thereof, or a tissue; and (2) pharmaceutical compositions for enhancing the inhibitory, therapeutic, or preventive effect of immunosuppressive agents on graft rejection (immunological rejection) accompanying the transplantation of an organ, a portion thereof, or a tissue.

BACKGROUND

Due to the recent revision of laws on organ transplantation, a few organ transplants from brain dead patients have been performed in Japan. In one case, seven patients received such benefits from one donor. Hereafter, organ transplantations are expected to increase.

On the other hand, Japanese patients affected by severe cardiovascular diseases, such as, hepatic diseases (acute hepatic failure, hepatic cirrhosis, etc.), cardiac diseases (severe heart failure, cardiomyopathy, cardiac hypertrophy, etc.), renal diseases (renal failure, chronic glomerulonephritis, diabetic nephropathy, pyelonephritis, etc.), pulmonary diseases (pulmonary dysfunction of both lungs, etc.), and pancreatic diseases (treatment of diabetic patients), for whom organ transplantation is vital for therapy, are estimated to increase each year by about 600 heart patients, about 3,000 liver patients, and about 500 lung patients. While the legal aspect is being developed, the lack of transplantable organs is also a real problem that exists at the moment. Similarly, the lack of organs is a serious problem also in the United States, which is an advanced nation in terms of transplantation. In the United States, approximately 4,300 people (1999) are awaiting heart transplantations and approximately 43,000 people (1999) are awaiting renal transplantations. In reality, approximately 800 people and approximately 2,300 people die each year without being able to receive heart and kidney transplantations, respectively.

Tissue (such as skin, cornea and bone) or organ (such as liver, heart, kidney, lung and pancreas) transplantation includes: (1) autotransplantation (autologous transplantation), (2) isotransplantation, (3) allotransplantation, and (4) xenotransplantation.

Autotransplantation refers to the transplantation of a part of an individual to another part of the same individual, and an example is the case of treating a burn by grafting one's own normal skin to the affected area.

Isotransplantation is performed between homogeneous animals. In humans, such a transplantation is performed between monozygotic twins (for example, transplantation of one of the kidneys or liver tissues).

Allotransplantation is performed between two different individuals having different genetic backgrounds, and in humans, such a transplantation is performed between dizygotic twins or between individuals who have absolutely no blood relation to each other.

Xenotransplantation is performed between individuals of different animal species. An example is the case where a tissue or an organ of a chimpanzee or a pig is transplanted into a human.

As mentioned above, allotransplantations from brain dead patients are expected to increase due to the development of legislation relating to organ transplantation. However, in order to resolve the absolute lack of transplantable organs, various investigations are now being actively pursued aiming at practical applications of xenotransplantation, more specifically, the transplantation of tissues or organs from non-human mammals such as pigs to humans.

While the issue of the lack of transplantable tissues and organs is expected to be resolved by the development of laws on brain death and transplantation, and by the improvement of xenotransplantation techniques, there is another extremely large obstacle in treating diseases by allotransplantation and xenotransplantation. More specifically, the obstacle is severe immunological rejection (graft rejection) in recipients that occurs after the transplantation of tissues or organs from donors.

Graft rejection refers to various immune responses that try to reject and eliminate a graft (a part of a living body that is transplanted, a cell, a tissue, or an organ) from a donor whose genetic background is different to that of the recipient (i.e., allotransplantation or xenotransplantation) since the recipient recognizes the graft as a foreign substance. The immune responses that accompany this transplantation can be classified into: (1) hyper-acute rejection, which is a strong rejection occurring immediately after transplantation; (2) acute rejection, which is observed within a few months after transplantation; and (3) chronic rejection observed several months after transplantation. Furthermore, although cellular immunity due to immunocompetent cells represented by T cells, and humoral immunity due to antibodies occur in an intricately coordinated manner, the main response is by cellular immunity.

As a result of graft rejection, the graft ultimately becomes necrotic and falls off. Furthermore, the recipient develops not only severe systemic symptoms such as fever, leukocytosis and fatigue, but also swelling and tenderness at the transplantation site. Furthermore, severe complications such as infections may occur.

In particular, when transplanting a xenogenic graft such as that from a pig, the serious problem of hyper-acute rejection occurs whereby the graft is rejected within minutes.

A limited number of immunosuppressive agents that suppress the function of immunocompetent cells are used to suppress the immunological rejection (graft rejection) accompanying such transplantations, because the immunological rejection caused by allotransplantation is mainly due to cellular immunity. Such immunosuppressive agents include cyclosporin (CsA); tacrolimus (FK-506); azathioprine (AZ); mycophenolate mofetil (MMF); mizoribine (MZ); leflunomide (LEF); adrenocortical steroids (also known as adrenocortical hormones, corticosteroids, corticoids) such as prednisolon and methylprednisolon; sirolimus (also known as rapamycin); deoxyspergualin (DSG); and FTY720 (chemical name: 2-amino-2-[2-(4-octylphenyl) ethyl]-1,3-propanediol hydrochloride).

CTLA4 and CD28 which are molecules responsible for transducing costimulatory signals necessary for the activation of T cells (costimulatory signal transduction molecules), and especially CTLA4 drugs that use the soluble region of CTLA4 and the gene encoding it are also being clinically developed as immunosuppressive agents.

On the other hand, recently, similarly to CTLA4 and CD28 which are costimulatory signal-transducing molecules, a molecule called activation inducible lymphocyte immunomodulatory molecule (AILIM; human, mouse, and rat; Int. Immunol., 12(1), p. 51-55, 2000; also called Inducible costimulator (ICOS; human; Nature, 397(6716), p. 263-266, 1999); J. Immunol., 166(1), p. 1, 2001; J. Immunol., 165(9), p. 5035, 2000; Biochem. Biophys. Res. Commun., 276(1), p. 335, 2000; Immunity, 13(1), p. 95, 2000; J. Exp. Med., 192 (1), p. 53, 2000; Eur. J. Immunol., 30(4), p. 1040, 2000) was identified as the third costimulatory signal transduction molecule that transduces a second signal (costimulatory signal) necessary for the activation of lymphocytes such as T cells, and coupled with the signal, regulates the function of activated lymphocytes such as activated T cells.

Based on the findings from recent studies relating to this molecule, the AILIM molecule is predicted to be possibly involved in various diseases (for example, autoimmune diseases, allergies, and inflammations) caused by the activation of immunocompetent cells such as T cells (especially T cells). However, there are no reports whatsoever on the relationship between the functional modulation of the AILIM molecule and graft rejection (immunological rejection) accompanying tissue or organ transplantation, as well as attempts to suppress, treat, or prevent such rejection reactions accompanying tissue or organ transplantation by modulating the activity of the AILIM molecule.

In addition, a novel molecule called B7h, B7RP-1, GL50, or LICOS which is considered to be a ligand interacting with the costimulatory signal transduction molecule AILIM has been identified very recently (Nature. Vol. 402, No. 6763, pp. 827-832, 1999; Nature Medicine, Vol. 5, No. 12, pp. 1365-1369, 1999; J. Immunology, Vol. 164, pp. 1653-1657, 2000; Curr. Biol., Vol. 10, No. 6, pp. 333-336, 2000).

The identification of these two kinds of novel molecules, namely AILIM (ICOS) and B7RP-1 (B7h, GL50, LICOS), revealed that, in addition to the known first and second signal transduction pathways between CD28 and CD80 (B7-1)/CD86 (B7-2) and between CTLA4 and CD80 (B7-1)/CD 86 (B7-2), there is a novel third costimulatory signal transduction pathway that is essential for the above mentioned activation of lymphocytes such as T cells and the control of the function of activated T cells, which functions through the interaction between AILIM (ICOS) and B7RP-1 (B7h, GL50, LICOS).

Exhaustive studies are in progress on the biological functions of these novel molecules, the regulation of functions of lymphocytes such as T cells through the third costimulatory signal transduction by the molecules, and the relationship between the novel signal transduction and diseases.

BRIEF DESCRIPTION OF THE DRAWINGS

FIG. 1 shows the effect of an anti-AILIM antibody and/or an immunosuppressive agent on the suppression of immunological rejection (graft rejection) accompanying organ transplantation, using as an index, the prolongation of graft survival in a recipient who was transplanted with a liver from a donor.

FIG. 2 shows the effect of suppression of immunological rejection (graft rejection) that occurs accompanying organ transplantation by anti-AILIM antibody and/or an immunosuppressive agent, which uses as an index the extended days of graft survival of the transplanted liver from a donor in a recipient.

FIG. 4 is a photograph showing the degree of infiltration of AILIM-expressing cells into a transplanted heart.

FIG. 5 shows the effect of suppression of immunological rejection (graft rejection) that occurs accompanying organ transplantation by anti-AILIM antibody and/or AdCTLA4-Ig, which uses as an index the extension of days of graft survival of the transplanted heart from a donor in a recipient.

FIG. 6 shows the effect of an anti-AILIM used in combination with AdCTLA4-Ig on the suppression of immunological rejection (graft rejection) accompanying organ transplantation, using as an index, the presence or absence of graft survival of a transplanted heart (primary heart transplantation and secondary heart transplantation) and transplanted skin (primary skin transplantation) in a recipient.

DETAILED DESCRIPTION

Figure 3:
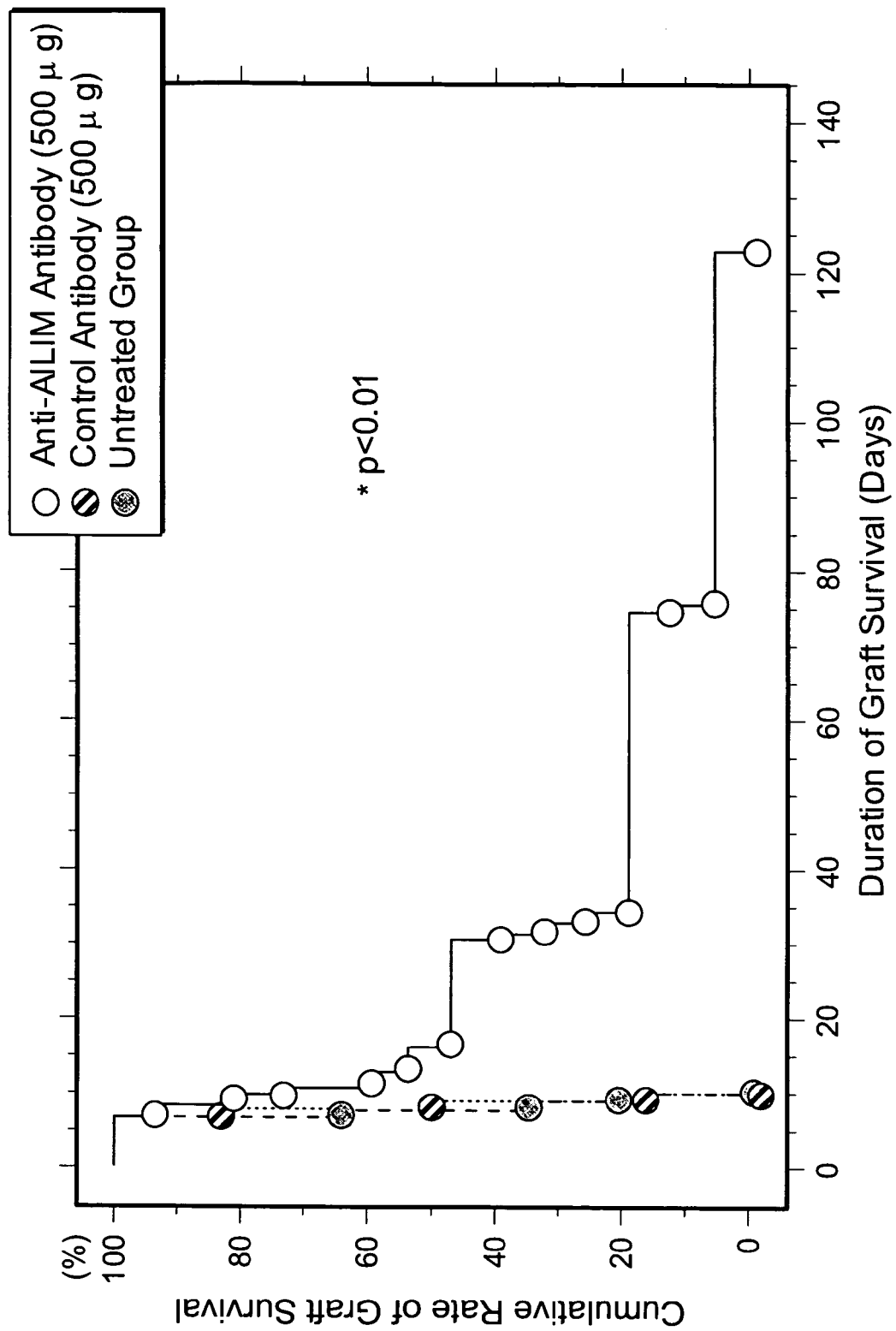
FIG. 3 shows the effect of suppression of immunological rejection (graft rejection) that occurs accompanying organ transplantation by anti-AILIM antibody (otherwise called anti-ICOS antibody), which uses as an index the extension of days of graft survival of the transplanted heart from a donor in a recipient.

More specifically, an objective of the present invention is to provide methods and pharmaceutical agents that suppress, treat, or prevent immunological rejections (graft rejection) accompanying the transplantation of a tissue or an organ (allotransplantation or xenotransplantation) by using medical and pharmaceutical techniques (for example, pharmaceutical agents such as low-molecular weight compounds and antibodies) to modulate the biological function of a novel molecule, AILIM, which is considered to transduce a second signal (costimulatory signal) necessary for activating lymphocytes such as T cells, and coupled with the signal, modulates the function of activated lymphocytes such as activated T cells.

Another objective is to provide methods for enhancing the suppressive effect on graft rejection by existing immunosuppressive agents (cyclosporin, azathioprine, adrenocortical steroids, FK-506, etc.) using such pharmaceutical agents that modulate the biological function of AILIM (for example, pharmaceutical agents such as low-molecular weight compounds and antibodies).

As a result of exhaustive research relating to the biological function of mammalian AILIM and a method for suppressing immunological rejection (graft rejection), which is a serious problem accompanying transplantation (allotransplantation or xenotransplantation) of grafts (cells, a tissue, or an organ), the present inventors found that (1) pharmaceutical agents that modulate the function of AILIM significantly suppress the immunological rejection (graft rejection) accompanying transplantation of tissue(s) or organ(s), and (2) the suppressive effect of existing immunosuppressive agents on graft rejection is enhanced by using pharmaceutical agents that modulate the function of AILIM, and completed the present invention.

A pharmaceutical composition of the present invention is useful as a pharmaceutical for modulating various reactions in vivo in which the transduction of a costimulatory signal to AILIM-expressing cells mediated by AILIM is involved (for example, proliferation of AILIM-expressing cells, production of cytokine(s) by AILIM-expressing cells, immune cytolysis or apoptosis of AILIM-expressing cells, and the activity to induce antibody-dependent cellular cytotoxicity against AILIM-expressing cells), and/or as a pharmaceutical for preventing the onset and/or progression of various diseases in which the signal transduction mediated by AILIM is involved, and for the treatment or prophylaxis of the diseases.

Specifically, a pharmaceutical composition of the present invention can modulate (suppress or promote) the proliferation of AILIM-expressing cells, or can modulate (inhibit or promote) the production of cytokines (for example, interferon γ, or interleukin 4) by AILIM-expressing cells, and can prevent various disease conditions triggered by various physiological phenomena in which the signal transduction mediated by AILIM is involved, and enables the treatment or prevention of various diseases.

The use of a pharmaceutical composition of this invention enables the suppression, prevention, and/or treatment of immunological rejection (graft rejection), which is a serious problem in therapies where an organ (liver, heart, lung, kidney, pancreas, etc.) a portion thereof, or a tissue (such as skin, cornea, and bone) from a donor is transplanted (allotransplanted or xenotransplanted) to a recipient affected by a severe cardiovascular disease.

Furthermore, the use of a pharmaceutical composition of this invention enables the enhancement of the graft rejection-suppressive effect of existing immunosuppressive agents administered to suppress immunological rejection in such transplant therapies.

More specifically, the present inventions are as follows:

(1) A pharmaceutical composition for suppressing, treating, or preventing graft rejection accompanying the transplantation of an organ, a portion thereof, or a tissue, said composition comprising a substance having an activity to modulate signal transduction mediated by AILIM, and a pharmaceutically acceptable carrier.

(2) A pharmaceutical composition for enhancing the effect of one or more immunosuppressive agent(s) on the suppression, treatment, or prevention of graft rejection accompanying the transplantation of an organ, a portion thereof, or a tissue, said composition comprising a substance having an activity to modulate signal transduction mediated by AILIM, and a pharmaceutically acceptable carrier.

(3) The pharmaceutical composition of (2), wherein said immunosuppressive agent is one or more therapeutic agent(s) selected from the group consisting of azathioprine, adrenocortical steroid, cyclosporin, mizoribine and tacrolimus (FK-506), mycophenolate mofetil, leflunomide, sirolimus, deoxyspergualin, FTY720, and CTLA4 drug.

(4) The pharmaceutical composition of any one of (1) to (3), wherein said transplantation is allotransplantation.

(5) The pharmaceutical composition of any one of (1) to (3), wherein said transplantation is xenotransplantation.

(6) The pharmaceutical composition of any one of (1) to (5), wherein said organ is the liver, heart, kidney, lung, or pancreas.

(7) The pharmaceutical composition of any one of (1) to (5), wherein said tissue is the skin, cornea, or bone tissue.

(8) The pharmaceutical composition of any one of (1) to (7), wherein said substance is a proteinaceous substance.

(9) The pharmaceutical composition of (8) wherein said proteinaceous substance is selected from group consisting of:

a) an antibody that binds to AILIM, or a portion of said antibody;

b) a polypeptide comprising the whole or a portion of an extracellular region of AILIM;

c) a fusion polypeptide comprising the whole or a portion of an extracellular region of AILIM, and the whole or a portion of a constant region of the immunoglobulin heavy chain; and, d) a polypeptide that binds to AILIM.

(10) The pharmaceutical composition of any one of (1) to (7), wherein said substance is a non-proteinaceous substance.

(11) The pharmaceutical composition of (10) wherein said non-proteinaceous substance is DNA, RNA, or a chemically synthesized compound.

The present inventions are described in detail herein below by defining the terms and the methods for producing the substances used in this invention.

Herein, the term "mammal" means a human, cow, goat, rabbit, mouse, rat, hamster, and guinea pig; preferred is a human, cow, rat, mouse, or hamster, and particularly preferred is a human.

"AILIM" of this invention is an abbreviation for "Activation Inducible Lymphocyte Immunomodulatory Molecule" and denotes a cell surface molecule of a mammal having the structure and function described in previous reports (J. Immunol., 166(1), p. 1, 2001; J. Immunol., 165(9), p. 5035, 2000; Biochem. Biophys. Res. Commun., 276(1), p. 335, 2000; Immunity, 13(1), p. 95, 2000; J. Exp. Med., 192(1), p. 53, 2000; Eur. J. Immunol., 30(4), p. 1040, 2000; Int. Immunol., 12(1), p. 51, 2000; Nature, 397(6716), p. 263, 1999; GenBank Accession Number: BAA82129 (human); BAA82128 (rat); BAA82127 (rat variant); BAA82126 (mouse)).

Especially preferably, the term denotes AILIM derived from a human (for example, International Immunology, Vol. 12, No. 1, p. 51-55, 2000).

This AILIM is also called ICOS (Nature, Vol. 397, No. 6716, p. 263-266, 1999) or JTT-1 antigen/JTT-2 antigen (Unexamined Published Japanese Patent Application No. (JP-A) Hei 11-29599, International Patent Application No. WO98/38216), and these molecules mutually refer to the same molecule.

In addition, "AILIM" as referred to in this invention includes a polypeptide having the amino acid sequences of AILIM from each mammal described in previously reported literature, and especially preferably, also a polypeptide having substantially the same amino acid sequence as that of human AILIM. Furthermore, human AILIM variants similar to the previously identified AILIM variant derived from rat (GenBank Accession Number: BAA82127) are also included in the "AILIM" of this invention.

Herein, the expression "having substantially the same amino acid sequence" means that "AILIM" of the present invention includes a polypeptide having an amino acid sequence in which multiple amino acids, preferably 1 to 10 amino acids, particularly preferably 1 to 5 amino acids, have been substituted, deleted, and/or modified, and polypeptides having an amino acid sequences in which multiple amino acids, preferably 1 to 10 amino acids, particularly preferably 1 to 5 amino acids, have been added, as long as the polypeptides have substantially the same biological properties as the polypeptide comprising the amino acid sequence shown in previous reports.

Such substitutions, deletions, or insertions of amino acids can be achieved according to the usual method (Experimental Medicine: SUPPLEMENT, "Handbook of Genetic Engineering" (1992), etc.).

Examples are synthetic oligonucleotide site-directed mutagenesis (gapped duplex method), point mutagenesis by which a point mutation is introduced at random by treatment with nitrite or sulfite, the method by which a deletion mutant is prepared with Bal31 enzyme and so on, cassette mutagenesis, linker scanning method, misincorporation method, mismatch primer method, DNA segment synthesis method, etc.

Synthetic oligonucleotide site-directed mutagenesis (gapped duplex method) can be performed, for example, as follows. The region one wishes to mutagenize is cloned into a M13 phage vector having an amber mutation to prepare a single-stranded phage DNA. After RF I DNA of M13 vector having no amber mutation is linearized by restriction enzyme treatment, the DNA is mixed with the single-stranded phage DNA mentioned above, denatured, and annealed thereby forming a "gapped duplex DNA." A synthetic oligonucleotide into which mutations are introduced is hybridized with the gapped duplex DNA and a closed-circular double-stranded DNA is prepared by reacting with DNA polymerase and DNA ligase. *E. coli* mutS cells, deficient in mismatch repair activity, are transfected with this DNA. *E. coli* cells having no suppressor activity are infected with the grown phages, and only phages having no amber mutations are screened.

The method by which a point mutation is introduced with nitrite utilizes, for example, the principle as mentioned below. If DNA is treated with nitrite, nucleotides are deaminated to change adenine into hypoxanthine, cytosine into uracil, and guanine into xanthine. If deaminated DNA is introduced into cells, "A:T" and "G:C" are replaced with "G:C" and "A:T", respectively, because hypoxanthine, uracil, and xanthine base pair with cytosine, adenine, and thymine, respectively, in DNA replication. Actually, single-stranded DNA fragments treated with nitrite are hybridized with "gapped duplex DNA", and thereafter, mutant strains are separated by manipulating in the same way as synthetic oligonucleotide site-directed mutagenesis (gapped duplex method).

The term "cytokine" as in "production of a cytokine by AILIM-expressing cells" in the present invention means an arbitrary cytokine produced by AILIM-expressing cells (especially, T cells).

Examples of T cells are T cells of the Th1 type and Th2 type, and a cytokine of the present invention specifically means a cytokine produced by T cells of the Th1 type and/or an arbitrary cytokine produced by T cells of the Th2 type.

Cytokines produced by T cells of the Th1 type include IFN-γ, IL-2, TNF, IL-3, and cytokines produced by T cells of Th2 type include IL-3, IL-4, IL-5, IL-10, and TNF (Cell, Vol. 30, No. 9, pp. 343-346, 1998).

The term "substance" as used in the present invention, specifically a "substance having an activity to modulate the signal transduction mediated by AILIM", and more specifically "a substance having an activity to inhibit the proliferation of AILIM-expressing cells, or to inhibit the production of a cytokine by AILIM-expressing cells" means a naturally-occurring substance or an artificially-prepared arbitrary substance.

Herein, the expression "signal transduction mediated by AILIM" means signal transduction through AILIM, leading to a change of any phenotype in the AILIM-expressing cells described above or in the following Examples (a change in cell proliferation, activation of cells, inactivation of cells, apoptosis, and/or the ability to produce an arbitrary cytokine from AILIM-expressing cells).

"The substance" can be mainly classified into a "proteinaceous substance" and a "non-proteinaceous substance".

Examples of "proteinaceous substances" are the following polypeptides and antibodies (polyclonal antibodies, monoclonal antibodies, or portions of monoclonal antibodies).

When the substance is an antibody, it is preferably a monoclonal antibody. When the substance is a monoclonal antibody, it includes not only non-human mammal-derived monoclonal antibodies, but also the following recombinant chimeric monoclonal antibodies, recombinant humanized monoclonal antibodies, and human monoclonal antibodies.

When the substance is a polypeptide, it includes the following polypeptides, polypeptide (oligopeptide) fragments, fusion polypeptides, and chemically modified polypeptides. Examples of oligopeptides are peptides comprising 5 to 30 amino acids, preferably 5 to 20 amino acids. A chemical modification can be designed depending on various purposes, for example, to increase half-life in blood in the case of administering in vivo, or to increase tolerance against degradation, or increase absorption in the digestive tract in oral administrations.

Examples of polypeptides are as follows:
(1) A polypeptide comprising the whole or a portion of an extracellular region of AILIM;
(2) A fusion polypeptide comprising the whole or a portion of an extracellular region of AILIM, and the whole or a portion of a constant region of the immunoglobulin heavy chain; or
(3) A polypeptide that binds to AILIM.

Examples of "non-proteinaceous substances" are DNA, RNA, and chemically synthesized compounds.

Here, "DNA" means "DNA useful as an antisense DNA drug comprising a partial nucleotide sequence of a DNA encoding the above AILIM (preferably human AILIM), or chemically modified DNA thereof, that may be designed based on the DNA (cDNA or genomic DNA) encoding the AILIM". Specifically, the antisense DNA can inhibit the transcription of DNA encoding AILIM into mRNA, or the translation of the mRNA into a protein by hybridizing to the DNA or RNA encoding AILIM.

The phrase "partial nucleotide sequence" as referred to herein refers to a partial nucleotide sequence comprising an arbitrary number of nucleotides in an arbitrary region. A partial nucleotide sequence includes 5 to 100 consecutive nucleotides, preferably 5 to 70 consecutive nucleotides, more preferably 5 to 50 consecutive nucleotides, and even more preferably, 5 to 30 consecutive nucleotides.

When the DNA is used as an antisense DNA drug, the DNA sequence can be chemically modified in part in order to extend the half-life (stability) in blood when the DNA is administered to patients, to increase the intracytoplasmic-membrane permeability of the DNA, or to increase the degradation resistance or the absorption of orally administered DNA in the digestive organs. Chemical modifications include, for example, the modification of a phosphate bond, a ribose, a nucleotide, the sugar moiety, and the 3' end and/or the 5' end in the structure of an oligonucleotide DNA.

Modifications of phosphate bonds include, for example, the conversion of one or more bonds to phosphodiester bonds (D-oligo), phosphorothioate bonds, phosphorodithioate bonds (S-oligo), methyl phosphonate (MP-oligo) bonds, phosphoroamidate bonds, non-phosphate bonds or methyl phosphonothioate bonds, or combinations thereof. Modification of a ribose includes, for example, the conversion to 2'-fluororibose or 2'-O-methylribose. Modification of a nucleotide includes, for example, the conversion to 5-propynyluracil or 2-aminoadenine.

Here, "RNA" means "RNA useful as an antisense RNA drug comprising a partial nucleotide sequence of a RNA encoding the above AILIM (preferably human AILIM), or chemically modified RNA thereof, that may be designed based on the RNA encoding the AILIM". The antisense RNA can inhibit the transcription of the DNA encoding AILIM into mRNA, or the translation of the mRNA into a protein by hybridizing to the DNA or RNA encoding AILIM.

The phrase "partial nucleotide sequence" as employed herein, refers to a partial nucleotide sequence comprising an arbitrary number of nucleotides in an arbitrary region. A partial nucleotide sequence includes 5 to 100 consecutive nucleotides, preferably 5 to 70 consecutive nucleotides, more preferably 5 to 50 consecutive nucleotides, and even more preferably 5 to 30 consecutive nucleotides.

The antisense RNA sequence can be chemically modified in part in order to extend the half-life in blood when the RNA is administered to patients, to increase the intracytoplasmic-membrane permeability of the RNA, or to increase the degradation resistance or the absorption of orally administered RNA in digestive organs. Chemical modifications include modifications such as those that apply to the above antisense DNA.

Examples of "a chemically synthesized compound" are an arbitrary compound excluding the above DNA, RNA and proteinaceous substances, having a molecular weight of about 100 to about 1000, or less, preferably a compound having a molecular weight of about 100 to about 800, and more preferably a molecular weight of about 100 to about 600.

The term "polypeptide" included in the definition of the above "substance" means a portion (a fragment) of a polypeptide chain constituting AILIM (preferably human AILIM), preferably the whole or a portion of an extracellular region of the polypeptide constituting AILIM (1 to 5 amino acids may be optionally added into the N-terminus and/or C-terminus of the region).

AILIM according to the present invention is a transmembrane molecule penetrating the cell membrane, comprising 1 or 2 polypeptide chains.

Herein, a "transmembrane protein" means a protein that is connected to the cell membrane through a hydrophobic peptide region that penetrates the lipid bilayer of the membrane once or several times, and whose structure is, as a whole, composed of three main regions, that is, an extracellular region, a transmembrane region, and a cytoplasmic region, as seen in many receptors or cell surface molecules. Such a transmembrane protein constitutes each receptor or cell surface molecule as a monomer, or as a homodimer, heterodimer or oligomer coupled with one or several chains having the same or different amino acid sequence(s).

Here, an "extracellular region" means the whole or a portion of a partial structure (partial region) of the entire structure of the above-mentioned transmembrane protein where the partial structure exists outside of the membrane. In other words, it means the whole or a portion of the region of the transmembrane protein excluding the region incorporated into the membrane (transmembrane region) and the region existing in the cytoplasm following the transmembrane region (cytoplasmic region).

"A fusion polypeptide" included in the above "proteinaceous substance" is a fusion polypeptide comprising the whole or a portion of the extracellular region of a polypeptide constituting AILIM (preferably human AILIM), and the whole or a portion of the constant region of immunoglobulin heavy chain (Ig, preferably human Ig). Preferably, the fusion polypeptide is a fusion polypeptide having the extracellular region of AILIM and a portion of the constant region of human IgG heavy chain, and particularly preferably, a fusion polypeptide of the extracellular region of AILIM and a region (Fc) of human IgG heavy chain comprising a hinge region, $C_H2$ domain and $C_H3$ domain. As an IgG, IgG1 is preferable, and as AILIM, human, mouse, or rat AILIM is preferable (preferably human).

The expression "the whole or a portion of the constant region of immunoglobulin (Ig) heavy chain" as used herein means the constant region or the Fc region of human-derived immunoglobulin heavy chain (H chain), or a portion thereof. The immunoglobulin can be any immunoglobulin belonging to any class and any subclass. Specifically, the immunoglobulin includes IgGs (IgG1, IgG2, IgG3, and IgG4), IgM, IgAs (IgA1 and IgA2), IgD, and IgE. Preferably, the immunoglobulin is IgG (IgG1, IgG2, IgG3, or IgG4), or IgM. Examples of particularly preferable immunoglobulins of the present invention are those belonging to human-derived IgGs (IgG1, IgG2, IgG3, or IgG4).

Immunoglobulin has a Y-shaped structural unit in which four chains composed of two homologous light chains (L chains) and two homologous heavy chains (H chains) are connected through disulfide bonds (S—S bonds). The light chain is composed of the light chain variable region ($V_L$) and the light chain constant region ($C_L$). The heavy chain is composed of the heavy chain variable region ($V_H$) and the heavy chain constant region ($C_H$).

The heavy chain constant region is composed of some domains having amino acid sequences unique to each class (IgG, IgM, IgA, IgD, and IgE) and each subclass (IgG1, IgG2, IgG3, and IgG4, IgA1, and IgA2).

The heavy chain of IgGs (IgG1, IgG2, IgG3, and IgG4) is composed of $V_H$, $C_H1$ domain, hinge region, $C_H2$ domain, and $C_H3$ domain in this order from the N-terminus.

Similarly, the heavy chain of IgG1 is composed of $V_H$, $C\gamma_11$ domain, hinge region, $C\gamma_12$ domain, and $C\gamma_13$ domain in this order from the N terminus. The heavy chain of IgG2 is composed Of $V_H$, $C\gamma_21$ domain, hinge region, $C\gamma_22$ domain, and $C\gamma_23$ domain in this order from the N-terminus. The heavy chain of IgG3 is composed of $V_H$, $C\gamma_31$ domain, hinge region, $C\gamma_32$ domain, and $C\gamma_33$ domain in this order from the N terminus. The heavy chain of IgG4 is composed of $V_H$, $C\gamma_41$ domain, hinge region, $C\gamma_42$ domain, and $C\gamma_43$ domain in this order from the N-terminus.

The heavy chain of IgA is composed of $V_H$, $C\alpha1$ domain, hinge region, $C\alpha2$ domain, and $C\square3$ domain in this order from the N-terminus.

Similarly, the heavy chain of IgA1 is composed of $V_H$, $C\alpha_11$ domain, hinge region, $C\alpha_12$ domain, and $C\alpha_13$ domain in this order from the N-terminus. The heavy chain of IgA2 is composed of $V_H$, $C\alpha_21$ domain, hinge region, $C\alpha_22$ domain, and $C\alpha_23$ domain in this order from the N-terminus.

The heavy chain of IgD is composed of $V_H$, $C\delta1$ domain, hinge region, $C\delta2$ domain, and $C\delta3$ domain in this order from the N-terminus.

The heavy chain of IgM is composed of $V_H$, $C\mu1$ domain, $C\mu2$ domain, $C\mu3$ domain, and $C\mu4$ domain in this order from the N-terminus and has no hinge region as seen in IgG, IgA, and IgD.

The heavy chain of IgE is composed of $V_H$, $C\epsilon1$ domain, $C\epsilon2$ domain, $C\epsilon3$ domain, and $C\epsilon64$ domain in this order from the N-terminus and have no hinge region as seen in IgG, IgA, and IgD.

If, for example, IgG is treated with papain, it is cleaved at a slightly N-terminal side beyond the disulfide bonds existing in the hinge region where the disulfide bonds connect the two heavy chains to generate two homologous Fabs, in which a heavy chain fragment composed of $V_H$ and $C_H1$ is connected to one light chain through a disulfide bond; and one Fc, in which two homologous heavy chain fragments composed of the hinge region, $C_H2$ domain, and $C_H3$ domain are connected through disulfide bonds (See "Immunology Illustrated", original 2nd ed., Nankodo, pp. 65-75 (1992); and "Focus of Newest Medical Science 'Recognition Mechanism of Immune System'", Nankodo, pp. 4-7 (1991); and so on).

Namely, "a portion of the constant region of immunoglobulin heavy chain" mentioned above means a portion of the constant region of an immunoglobulin heavy chain having the structural characteristics as mentioned above, and preferably, is a constant region without the C1 domain, or the Fc region. Specifically, an example thereof is a region composed of the hinge region, C2 domain, and C3 domain from each of IgG, IgA, and IgD, or is a region composed of C2 domain, C3 domain, and C4 domain from each of IgM and IgE. A particularly preferable example thereof is the Fc region of human-derived IgG1.

The fusion polypeptide mentioned above has the advantage of being extremely easy to purify by using affinity column chromatography using the property of protein A, which binds specifically to the immunoglobulin fragment, because the fusion polypeptide of the present invention has a portion of a constant region (for example Fc) of an immunoglobulin such as IgG as mentioned above as a fusion partner. Moreover, since various antibodies against the Fc of various immunoglobulins are available, an immunoassay for the fusion polypeptides can be easily performed with antibodies against the Fc.

An example of "a fusion polypeptide comprising the whole or a portion of the extracellular region of a polypeptide constituting AILIM and the whole or a portion of the constant region of immunoglobulin heavy chain" is a fusion protein between IgG-Fc and the extracellular region of mouse AILIM (see, e.g., PCT Publication No. No. WO98/38216 and European Patent Application No. EP0984023).

"A polypeptide that binds to AILIM" is encompassed in "a polypeptide" included in the definition of the above "substance".

A specific example of "a polypeptide that binds to AILIM" is the whole or a portion of a polypeptide comprising a known molecule called B7h, B7RP-1, GL50 or LICOS, which is a ligand that interacts with AILIM (Nature, Vol. 402, No. 6763, pp. 827-832, 1999; Nature Medicine, Vol. 5, No. 12, pp. 1365-1369, 1999; J. Immunology, Vol. 164, pp. 1653-1657, 2000; Curr. Biol., Vol. 10 No 6, pp. 333-336, 2000).

Preferably, the polypeptide is a polypeptide comprising the whole or a portion of an extracellular region of the above ligands (B7h, B7RP-1, GL50, LICOS), or a fusion polypeptide comprising the polypeptide and the whole or a portion of the constant region of immunoglobulin heavy chain (preferably human immunoglobulin). Here, the expressions "extracellular region" and "constant region of immunoglobulin heavy chain" have the same meanings as mentioned above.

The polypeptides, portions of the polypeptide (fragment), and fusion polypeptides mentioned above can be produced not only by recombinant DNA technology as mentioned below, but also by a method well known in the art such as a chemical synthetic method or a cell culture method, or a modified method thereof.

The "antibody" of the present invention can be a polyclonal antibody (antiserum) or a monoclonal antibody against mammalian AILIM (particularly preferably human AILIM) defined above, and preferably a monoclonal antibody.

Specifically, the antibody is an antibody having an activity to inhibit proliferation of AILIM-expressing cells by binding to AILIM, or to inhibit production of interferon-γ or interleukin-4 by AILIM-expressing cells through binding to AILIM.

The antibodies of the present invention can be natural antibodies obtained by immunizing mammals such as mice, rats, hamsters, guinea pigs, and rabbits with an antigen such as cells (natural cells, cell lines, tumor cells, etc.) expressing AILIM of the present invention, transformants prepared using recombinant DNA technology so as to overexpress AILIM on the surface thereof, polypeptides constituting AILIM, or the above-mentioned fusion polypeptides comprising the AILIM polypeptide or the extracellular region of AILIM. The antibodies of the present invention also include chimeric antibodies and humanized antibodies (CDR-grafted antibodies) that can be produced by recombinant DNA technology, and human antibodies that can be produced using human antibody-producing transgenic animals.

Monoclonal antibodies include those having any one isotype of IgG, IgM, IgA, IgD, or IgE. IgG or IgM is preferable.

A polyclonal antibody (antisera) or monoclonal antibody can be produced by known methods. Namely, a mammal, preferably, a mouse, rat, hamster, guinea pig, rabbit, cat, dog, pig, goat, horse, or cow, or more preferably, a mouse, rat, hamster, guinea pig, or rabbit is immunized, for example, with an antigen mentioned above with Freund's adjuvant, if necessary.

A polyclonal antibody can be obtained from the serum obtained from the animal so immunized. In addition, monoclonal antibodies are produced as follows. Hybridomas are prepared from the antibody-producing cells obtained from the animal so immunized and myeloma cells that are not capable of producing autoantibodies. The hybridomas are cloned, and clones producing the monoclonal antibodies showing a specific affinity to the antigen used for immunizing the mammal are screened.

Specifically, a monoclonal antibody can be produced as follows. Immunizations are performed by injecting or implanting once or several times an antigen mentioned above as an immunogen, if necessary, with Freund's adjuvant, subcutaneously, intramuscularly, intravenously, through the footpad, or intraperitoneally into a non-human mammal, specifically a mouse, rat, hamster, guinea pig, or rabbit, preferably a mouse, rat, or hamster (including a transgenic animal generated so as to produce antibodies derived from another animal such as a transgenic mouse producing human antibody mentioned below). Usually, immunizations are performed once to four times every one to fourteen days after the first immunization. Antibody-producing cells are obtained from the mammal so immunized in about one to five days after the last immunization. The frequency and interval of immunizations can be appropriately arranged depending on, for example, the property of the immunogen used.

Hybridomas that secrete a monoclonal antibody can be prepared by the method of Köhler and Milstein (Nature, Vol. 256, pp. 495-497 (1975)), or by a modified method thereof. Namely, hybridomas are prepared by fusing antibody-producing cells contained in a spleen, lymph node, bone marrow, or tonsil obtained from a non-human mammal immunized as mentioned above, preferably a spleen, with myelomas without an autoantibody-producing ability, which are derived from, preferably, a mammal such as a mouse, rat, guinea pig, hamster, rabbit, or human, or more preferably, a mouse, rat, or human.

For example, a mouse-derived myeloma P3/X63-AG8.653 (653), P3/NSI/1-Ag4-1 (NS-1), P3/X63-Ag8.U1 (P3U1), SP2/0-Ag14 (Sp2/0, Sp2), PAI, F0, NSO, or BW5147, rat-derived myeloma 210RCY3-Ag.2.3., or human-derived myeloma U-266AR1, GM1500-6TG-A1-2, UC729-6, CEM-AGR, D1R11, or CEM-T15 can be used as a myeloma for cell fusion.

Hybridomas producing monoclonal antibodies can be screened by cultivating hybridomas, for example, in microtiter plates and by measuring the reactivity of the culture supernatant in wells in which hybridoma growth is observed, to the immunogen used for the immunization mentioned above, for example, by an enzyme immunoassay such as RIA and ELISA.

Monoclonal antibodies can be produced from hybridomas by cultivating the hybridomas in vitro or in vivo such as in the ascites fluid of a mouse, rat, guinea pig, hamster, or rabbit, preferably a mouse or rat, more preferably mouse, and isolating the antibodies from the resulting culture supernatant or ascites fluid of a mammal.

Cultivating hybridomas in vitro can be performed depending on, e.g., the property of cells to be cultured, the object of the study, and the various conditions of the culture method, by using known nutrient media or any nutrient media derived from known basal media for growing, maintaining, and storing the hybridomas to produce monoclonal antibodies in the culture supernatant.

Examples of basal media are low calcium concentration media such as Ham'F12 medium, MCDB 153 medium, or low calcium concentration MEM medium, and high calcium concentration media such as MCDB104 medium, MEM medium, D-MEM medium, RPMI1640 medium, ASF104 medium, or RD medium. The basal media can contain, for example, sera, hormones, cytokines, and/or various inorganic or organic substances depending on the objective.

Monoclonal antibodies can be isolated and purified from the culture supernatant or ascites fluid mentioned above by saturated ammonium sulfate precipitation, euglobulin precipitation method, caproic acid method, caprylic acid method, ion exchange chromatography (DEAE or DE52), and affinity chromatography using an anti-immunoglobulin column or a protein A column.

A "recombinant chimeric monoclonal antibody" is a monoclonal antibody prepared by genetic engineering, and specifically means a chimeric antibody such as a mouse/human chimeric monoclonal antibody whose variable regions are derived from an immunoglobulin of a non-human mammal (mouse, rat, hamster, etc.) and whose constant regions are derived from human immunoglobulin.

A constant region derived from human immunoglobulin has an amino acid sequence unique to each isotype such as IgG (IgG1, IgG2, IgG3, IgG4), IgM, IgA, IgD, and IgE. The constant region of the recombinant chimeric monoclonal antibody can be that of human immunoglobulin belonging to any isotype. Preferably, it is a constant region of human IgG.

A chimeric monoclonal antibody can be produced, for example, as follows. Needless to say, the production method is not limited thereto.

A mouse/human chimeric monoclonal antibody can be prepared, referring to Experimental Medicine: SUPPLEMENT, Vol. 1.6, No. 10 (1988); and Examined Published Japanese Patent Application No. (JP-B) Hei 3-73280. Namely, it can be prepared by operably inserting the CH gene (C gene encoding the constant region of H chain) obtained from a DNA encoding human immunoglobulin downstream of active $V_H$ genes (rearranged VDJ gene encoding the variable region of H chain) obtained from a DNA encoding a mouse monoclonal antibody isolated from hybridoma producing the mouse monoclonal antibody, and the $C_L$ gene (C gene encoding the constant region of L chain) obtained from a DNA encoding human immunoglobulin downstream of active $V_L$ genes (rearranged VJ gene encoding the variable region of L chain) obtained from a DNA encoding a mouse monoclonal antibody isolated from hybridoma, into the same vector or a different vector in an expressible manner, followed by transforming host cells with the expression vector, and then by cultivating the transformants.

Specifically, DNAs are first extracted from mouse monoclonal antibody-producing hybridomas by the usual method, digested with appropriate restriction enzymes (for example, EcORI and HindIII), electrophoresed (using, for example, 0.7% agarose gel), and analyzed by Southern blotting. After an electrophoresed gel is stained, for example with ethidium bromide, and photographed, the gel is given marker positions, washed twice with water, and soaked in 0.25 M HCl for 15 minutes. Then, the gel is soaked in a 0.4 N NaOH solution for 10 minutes with gentle stirring. The DNAs are transferred to a filter for 4 hours by the usual method. The filter is recovered and washed twice with 2×SSC. After the filter is sufficiently dried, it is baked at 75° C. for 3 hours. After baking, the filter is treated with 0.1×SSC/0.1% SDS at 65° C. for 30 minutes. Then, it is soaked in 3×SSC/0.1% SDS. The filter obtained is treated with a prehybridization solution in a plastic bag at 65° C. for 3 to 4 hours.

Next, $^{32}$P-labeled probe DNA and a hybridization solution are added to the bag and reacted at 65° C. about 12 hours. After hybridization, the filter is washed under an appropriate salt concentration, reaction temperature, and time (for example, 2×SSC/0.1% SDS, room temperature, 10 minutes). The filter is put into a plastic bag with a small volume of 2×SSC and subjected to autoradiography after the bag is sealed.

Rearranged VDJ gene and VJ gene encoding H chain and L chain of a mouse monoclonal antibody are identified by Southern blotting mentioned above. The region comprising the identified DNA fragment is fractioned by sucrose density gradient centrifugation and inserted into a phage vector (for example, Charon 4A, Charon 28, λEMBL3, and λEMBL4). E. coli (for example LE392 and NM539) is transformed with the phage vector to generate a genomic library. The genomic library is screened by a plaque hybridization technique such as the Benton-Davis method (Science, Vol. 196, pp. 180-182 (1977)) using appropriate probes (H chain J gene, L chain (κ) J gene, etc.) to obtain positive clones comprising rearranged VDJ gene or VJ gene. By making a restriction map and determining the nucleotide sequence of the clones obtained, it is confirmed whether genes comprising the desired, rearranged $V_H$ (VDJ) gene or $V_L$ (VJ) gene have been obtained.

Separately, human $C_H$ gene and human $C_L$ gene used for chimerization are isolated. For example, when a chimeric antibody with human IgG1 is produced, Cλ1 gene is isolated as a $C_H$ gene, and Cκ gene as a $C_L$ gene. These genes can be isolated from a human genomic library with mouse Cγ1 gene and mouse Cκ gene, corresponding to human Cγ1 gene and human Cκ gene, respectively, as probes, taking advantage of the high homology between the nucleotide sequences of the mouse immunoglobulin gene and the human immunoglobulin gene.

Specifically, DNA fragments comprising human Cκ gene and an enhancer region are isolated from human λ Charon 4A HaeIII-AluI genomic library (Cell, Vol. 15, pp. 1157-1174 (1978)), for example, using a 3 kb HindIII-BamHI fragment of clone Ig146 (Proc. Natl. Acad. Sci. USA, Vol. 75, pp. 4709-4713 (1978)) and a 6.8 kb EcORI fragment of clone MEP10 (Proc. Natl. Acad. Sci. USA, Vol. 78, pp. 474-478 (1981)) as probes. In addition, for example, after human fetal hepatocyte DNA is digested with HindIII and fractioned by agarose gel electrophoresis, a 5.9 kb fragment is inserted into λ788 and then human Cγ1 gene is isolated with the probes mentioned above.

Using mouse $V_H$ gene, mouse $V_L$ gene, human $C_H$ gene, and human $C_L$ gene so obtained, and taking the promoter region and enhancer region into consideration, human $C_H$ gene is inserted downstream mouse $V_H$ gene and human $C_L$ gene is inserted downstream mouse $V_L$ gene into an expression vector such as pSV2gpt or pSV2neo with appropriate restriction enzymes and DNA ligase by the usual method. In this case, chimeric genes of mouse $V_H$ gene/human $C_H$ gene and mouse $V_L$ gene/human $C_L$ gene can be respectively inserted into the same expression vector or into different expression vectors.

Chimeric gene-inserted expression vector(s) thus prepared are introduced into myelomas that do not produce antibodies, for example, P3X63•Ag8•653 cells or SP210 cells by the protoplast fusion method, DEAE-dextran method, calcium phosphate method, or electroporation method. The transformants are screened by cultivating in media containing a drug corresponding to the drug resistance gene inserted into the expression vector and, then, cells producing desired chimeric monoclonal antibodies are obtained.

Desired chimeric monoclonal antibodies are obtained from the culture supernatant of antibody-producing cells thus screened.

The "humanized monoclonal antibody (CDR-grafted antibody)" of the present invention is a monoclonal antibody prepared by genetic engineering and specifically means a humanized monoclonal antibody wherein a portion or the whole of the complementarity-determining regions of the hypervariable region are derived from the complementarity-determining regions of the hypervariable region from a monoclonal antibody of an non-human mammal (mouse, rat, hamster, etc.), the framework regions of the variable region are derived from the framework regions of the variable region from human immunoglobulin, and the constant region is derived from a constant region from human-derived immunoglobulin.

The complementarity-determining regions of the hypervariable region exists in the hypervariable region in the variable region of an antibody and means three regions which directly and complementary binds to an antigen (complementarity-determining residues, CDR1, CDR2, and CDR3). The framework regions of the variable region mean four comparatively conserved regions lying upstream, downstream, or between the three complementarity-determining regions (framework region, FR1, FR2, FR3, and FR4).

In other words, a humanized monoclonal antibody means that in which all the regions except a portion or the whole of the complementarity-determining regions of the hypervariable region of a non-human mammal-derived monoclonal antibody have been replaced with their corresponding regions derived from a human immunoglobulin.

The constant region derived from human immunoglobulin has an amino acid sequence unique to each isotype such as IgG (IgG1, IgG2, IgG3, IgG4), IgM, IgA, IgD, and IgE. The constant region of a humanized monoclonal antibody in the present invention can be that from human immunoglobulin belonging to any isotype. Preferably, it is a constant region of human IgG. The framework regions of the constant region derived from human immunoglobulin are not particularly limited.

A humanized monoclonal antibody can be produced, for example, as follows. Needless to say, the production method is not limited thereto.

For example, a recombinant humanized monoclonal antibody derived from mouse monoclonal antibody can be prepared by genetic engineering, referring to Published Japanese Translation of International Publication (JP-WA) No. Hei 4-506458 and JP-A Sho 62-296890. Namely, at least one mouse H chain CDR gene and at least one mouse L chain CDR gene corresponding to the mouse H chain CDR gene are isolated from hybridomas producing mouse monoclonal antibody, and human H chain gene encoding the whole regions except human H chain CDR corresponding to mouse H chain CDR mentioned above and human L chain gene encoding the whole region except human L chain CDR corresponding to mouse L chain CDR mentioned above are isolated from human immunoglobulin genes.

The mouse H chain CDR gene(s) and the human H chain gene(s) so isolated are operably inserted into an appropriate vector so that they can be expressed. Similarly, the mouse L chain CDR gene(s) and the human L chain gene(s) are operably inserted into another appropriate vector so that they can be expressed. Alternatively, the mouse H chain CDR gene(s)/human H chain gene(s) and mouse L chain CDR gene(s)/human L chain gene(s) can be operably inserted into the same expression vector in an expressible manner. Host cells are transformed with the expression vector thus prepared to obtain transformants producing humanized monoclonal antibody. By cultivating the transformants, a desired humanized monoclonal antibody is obtained from the culture supernatant.

The "human monoclonal antibody" is an immunoglobulin in which the entire regions comprising the variable and constant region of H chain, and the variable and constant region of L chain constituting the immunoglobulin are derived from genes encoding human immunoglobulin.

The human antibody (preferably human monoclonal antibody) can be produced by well known methods, for example, in the same way as the production method of polyclonal or monoclonal antibodies mentioned above by immunizing, with an antigen, a transgenic animal prepared by integrating at least a human immunoglobulin gene into the gene locus of a non-human mammal such as a mouse.

For example, a transgenic mouse producing human antibodies is prepared by the methods described in Nature Genetics, Vol. 7, pp. 13-21 (1994); Nature Genetics, Vol. 15, pp. 146-156 (1997); JP-WA Hei 4-504365; JP-WA Hei 7-509137; Nikkei Science, No. 6, pp. 40-50 (1995); WO94/25585; Nature, Vol. 368, pp. 856-859 (1994); and JP-WA No. Hei 6-500233.

In addition, a recently developed technique for producing a human-derived protein from the milk of a transgenic cow or pig can also be applied (Nikkei Science, pp. 78-84 (April, 1997)).

The phrase "portion of an antibody" as used in the present invention means a partial region of a monoclonal antibody as mentioned above. It specifically means $F(ab')_2$, Fab', Fab, Fv (variable fragment of antibody), sFv, dsFv (disulfide stabilized Fv), or dAb (single domain antibody) (Exp. Opin. Ther. Patents, Vol. 6, No. 5, pp. 441-456 (1996)).

"$F(ab')_2$" and "Fab'" can be produced by treating immunoglobulin (monoclonal antibody) with a protease such as pepsin and papain, and means an antibody fragment generated by digesting the immunoglobulin near the disulfide bonds in the hinge regions existing between each of the two H chains. For example, papain cleaves IgG upstream of the disulfide bonds in the hinge regions existing between each of the two H chains to generate two homologous antibody fragments in which an L chain composed of $V_L$ (L chain variable region) and $C_L$ (L chain constant region), and an H chain fragment composed of $V_H$ (H chain variable region) and $C_H\gamma 1$ (γ1 region in the constant region of H chain) are connected at their C terminal regions through a disulfide bond. Each of such two homologous antibody fragments is called Fab'. Pepsin also cleaves IgG downstream of the disulfide bonds in the hinge regions existing between each of the two H chains to generate an antibody fragment slightly larger than the fragment in which the two above-mentioned Fab's are connected at the hinge region. This antibody fragment is called F(ab')$_2$.

The term "graft rejection" of the present invention refers to various immune responses that try to reject and eliminate a graft (a part of a living body that is transplanted; a cell, a tissue, or an organ) from a donor whose genetic background is different to that of the recipient (i.e., allotransplantation or xenotransplantation) since the recipient recognizes the graft as a foreign substance. The immune responses that accompany this transplantation can be classified into (1) hyper-acute rejection, which is a strong rejection occurring immediately after transplantation, (2) acute rejection, which is observed within a few months after transplantation, and (3) chronic rejection observed several months after transplantation. Furthermore, although cellular immunity due to immunocompetent cells represented by T cells, and humoral immunity due to antibodies occur in an intricately coordinated manner, the main response is by cellular immunity.

As a result of graft rejection, the graft ultimately becomes necrotic and falls off. Furthermore, the patient develops not only severe systemic symptoms such as fever, leukocytosis, and fatigue, but also swelling and tenderness at the transplantation site. Furthermore, severe complications such as infections may occur.

In particular, when transplanting a xenogenic graft such as that from a pig, the serious problem of hyper-acute rejection occurs, whereby the graft is rejected within minutes.

The term "graft" of this invention refers to "an organ or a portion thereof", or "a tissue" that is transplanted to a recipient mammal from a donor mammal.

The phrase "an organ or a portion thereof" relating to the transplantation of this invention refers to an arbitrary organ or a portion thereof that composes the living body of a mammal (preferably a human or a pig, and especially preferably a human). A preferred example is the liver, heart, lung, pancreas, kidney, large intestine, small intestine, or a portion thereof. Especially preferred is the liver, or a portion thereof.

The term "tissue" relating to the transplantation of this invention refers to an arbitrary tissue derived from the living body of a mammal (preferably a human or a pig, and preferably a human). A preferred example is a tissue such as skin, cornea, bone, or cardiac valve; however, it is not limited thereto.

The term "immunosuppressive agent" of this invention refers to any one or more existing immunosuppressive agents used to suppress an immunological rejection (graft rejection) in a recipient caused by transplantation of a graft in the clinical transplantation of cells, tissues, or organs, whose manufacture and sales as a pharmaceutical agent have been approved by a governmental organization; or any one or more of immunosuppressive agents that are currently used in clinical or preclinical trials, or will be used in clinical trials in the future, whose manufacture and sales as a pharmaceutical agent may be approved by a governmental organization after the trials.

Such immunosuppressive agents are used not only alone, but also in combination with 2, 3, or more agents. Therefore, the term "immunosuppressive agent" according to this invention includes the use of a single type of pharmaceutical agent, or combined use of a plurality of pharmaceutical agents (preferably used in combination with 2 or 3 agents).

Preferably, the immunosuppressive agent is, for example, one or more pharmaceutical agents selected from cyclosporin (CsA); tacrolimus (FK-506); azathioprine (AZ); mycophenolate mofetil (MMF); mizoribine (MZ); leflunomide (LEF); adrenocortical steroids (otherwise called adrenocortical hormones; corticosteroid; corticoid) such as prednisolon and methylprednisolon; sirolimus (otherwise called rapamycin); deoxyspergualin (DSG); FTY720 (chemical name: 2-amino-2-[2-(4-octylphenyl)ethyl]-1,3-propanediol hydrochloride), and a "CTLA4 drug" described below. Either one or both of tacrolimus (FK-506) and cyclosporin are especially preferable.

The term "CTLA4 drug" of this invention refers to a medicament which contains as an active ingredient (1) a polypeptide comprising the full length (including molecules having practically the same amino acid sequence), or the whole or a portion of the extracellular region of human CTLA4 (cytotoxic T lymphocyte-associated antigen 4; <amino acid sequence> GenBank Accession No. NP 005205; <cDNA> GenBank Accession No. NM 005214); (2) a fusion polypeptide comprising the whole or a portion of the extracellular region of human CTLA4, and the whole or a portion of another protein (especially preferably, the whole or a portion of the constant region of human immunoglobulin heavy chain) (hereinafter, abbreviated as CTLA4-IgFc or CTLA4-Ig); or (3) a DNA which may provide to a mammal (especially preferably a human) the polypeptide of (1) or the fusion polypeptide of (2), or a vector comprising the DNA (especially preferable is a plasmid generally used in gene therapy, or a viral vector derived from a virus (retrovirus, adenovirus, adeno-associated virus, etc.), or such).

Herein, each of the terms/phrases such as "extracellular region," "a portion," "constant region of the immunoglobulin heavy chain," "fusion polypeptide," and "practically the same" has the same meaning as defined above.

There are a number of reports on the significant immunosuppressive effect of the aforementioned CTLA4-Ig. For example, the high immunosuppressive effect of Y100F (tyrosine of position 100 is substituted with alanine) developed by Bristol-Myers Squibb/Repligen has been confirmed from various animal experiments, and this product is also included as one of the CTLA4 drugs of this invention (Igaku no Ayumi, Vol. 194, No. 14, p. 1195-1200, 2000; J. Clin. Invest., Vol. 103, p. 1223-1225, 1999; N. Engl. J. Med., Vol. 335, p. 1369-1377, 1996; J. Exp. Med., Vol. 178, p. 1801-1806, 1993; Blood, Vol. 94, p. 2523-2529, 1999; Nature Med., Vol. 6, p. 464-469, 2000; Blood, Vol. 83, p. 3815-3823, 1995; J. Clin. Invest., Vol. 2, p. 473-482, 1998; Blood, Vol. 85, p. 2607-2612, 1995; N. Engl. J. Med., Vol. 340, p. 1704-1714, 1999; N. Engl. J. Med. Vol. 335, p. 1369-1377, 1996; J. Clin. Invest., Vol. 103, p. 1243-1252, 1999).

The phrase "pharmaceutically acceptable carrier" of this invention includes an excipient, a diluent, a filler, a decomposing agent, a stabilizer, a preservative, a buffer, an emulsifier, an aromatic agent, a colorant, a sweetener, a viscosity-increasing agent, a flavor, a solubility-increasing agent, or some other additive. Using one or more of such carriers, a pharmaceutical composition can be formulated into tablets, pills, powders, granules, injections, solutions, capsules, troches, elixirs, suspensions, emulsions, syrups, etc.

The pharmaceutical composition can be administered orally or parenterally. Other forms for parenteral administration include a solution for external application, suppository for rectal administration, and pessary, prescribed by the usual method, which comprises one or more active ingredients.

The dosage can vary depending on the age, sex, weight, and symptoms of a patient, effect of treatment, administration route, period of treatment, the kind of active ingredient (the "substance" according to the present invention, mentioned above) contained in the pharmaceutical composition, etc. Usually, the pharmaceutical composition can be administered to an adult in a dose of 10 μg to 1000 mg (or 10 μg to 500 mg) per one administration. Depending on various conditions, a dosage less than that mentioned above may be sufficient in some cases and a dosage more than that mentioned above may be necessary in others.

In the case of an injection, it can be produced by dissolving or suspending an antibody in a non-toxic, pharmaceutically acceptable carrier such as physiological saline or commercially available distilled water for injection adjusting the concentration in the range of 0.1 μg antibody/ml carrier to 10 mg antibody/ml carrier. The injection thus produced can be administered to a human patient in need of treatment in the dose range of 1 μg to 100 mg/kg body weight, preferably in the range of 50 μg to 50 mg/kg body weight, one or more times a day. Examples of administration routes are medically appropriate administration routes such as intravenous injection, subcutaneous injection, intradermal injection, intramuscular injection, intraperitoneal injection, or such, preferably intravenous injection.

The injection can also be prepared into a non-aqueous diluent (for example, propylene glycol, polyethylene glycol, vegetable oil such as olive oil, and alcohol such as ethanol), suspension, or emulsion.

The injection can be sterilized by filtration with a bacteria-filtering filter, by mixing a bacteriocide, or by irradiation. The injection can be produced in such a manner that it is prepared at the time of use. Namely, it is freeze-dried to be a sterile solid composition that can be dissolved in sterile distilled water for injection or another solvent before use.

The pharmaceutical composition of the present invention is extremely useful for the suppression, prevention, and/or treatment of immunological rejection (graft rejection), which is a serious problem in therapies where an organ (liver, heart, lung, kidney, pancreas, etc.) or a portion thereof, or a tissue (such as skin, cornea, and bone) from a donor is transplanted (allotransplanted or xenotransplanted) to a recipient affected by a severe cardiovascular disease.

Furthermore, the pharmaceutical composition of this invention can increase the effect of the suppression of graft rejection (immunological rejection) by existing immunosuppressive agents administered to suppress graft rejection during such transplant therapies when the pharmaceutical composition is used in combination with the immunosuppressive agents.

Unless otherwise defined, all technical and scientific terms used herein have the same meaning as commonly understood by one of ordinary skill in the art to which this invention belongs. Suitable methods and materials are described below, although methods and materials similar or equivalent to those described herein can also be used in the practice or testing of the present invention. All publications, patent applications, patents, and other references mentioned herein are incorporated by reference in their entirety. In case of conflict, the present specification, including definitions, will control. In addition, the materials, methods, and examples are illustrative only and not intended to be limiting.

The following are examples of the practice of the invention. They are not to be construed as limiting the scope of the invention in any way.

EXAMPLES

Example 1

Suppression of Graft Rejection by an AILIM Modulating Substance in Liver Transplantation <1> Materials and Methods <1-1> Animals Adult Lewis rats (male, 210-250 g) and DA rats (male, 210-250 g) were used as recipients and donors, respectively.

<1-2> Anti-Rat AILIM Monoclonal Antibody

A monoclonal antibody purified from ascites fluid or the culture supernatant obtained by culturing in vitro or in vivo the previously reported hybridoma named "JTT-1" (this hybridoma has been internationally deposited on Oct. 11, 1996 at the National Institute of Bioscience and Human-Technology, Advanced Industrial Science and Technology, Ministry of Economy, Trade and Industry, which is an international depositary agency certified under the Budapest Treaty. International Accession No.: FERM BP-5707) that produces a mouse anti-rat AILIM monoclonal antibody (mouse anti-rat JTT-1 antigen monoclonal antibody) was used (JP-A Hei 11-29599 (Examples 1 and 2), and International Patent Application No. WO98/38216 (Examples 1 and 2)). Hereinafter, this antibody is simply referred to as "anti-AILIM antibody".

<1-3> Liver Transplantation

Following the previously reported method of Kamada et al., livers of donor DA rats were transplanted into recipient Lewis rats (Surgery, 93, p. 64, 1983; Transplantation, 30, p. 43, 1980; Transplantation, 28, p. 47, 1979).

Specifically, livers obtained from DA rats were washed by flushing ice-cooled sterilized distilled water from the portal vein. Next, transplantation of the livers to the recipient Lewis rats was initiated by suturing the supra-hepatic vena cava. Then, by using the cuff technique, the portal vein and the infra-hepatic vena cava were sutured (Transplant. Proc., 19, p. 1158, 1987; Transplantation, 43, p. 745, 1987).

If the recipient rats died within 3 days after completion of the transplantation, this was determined to be a technical failure of the transplantation. As a result, the success rate of the transplantation was 95%.

<1-4> Administration of the Anti-AILIM Antibody and/or an Immunosuppressive Agent After completion of transplantation, the anti-AILIM antibody and/or the immunosuppressive agent FK-506 were administered to each of the Lewis rats (each group containing 5-9 animals) in the doses and at the timing described below. The day on which transplantation was completed was counted as day zero (0).

The group to which neither the anti-AILIM antibody nor the immunosuppressive agent FK-506 were administered was used as the control.

1. Anti-AILIM antibody (1 mg/kg; intravenous injection; day 0)
2. Anti-AILIM antibody (1 mg/kg; intravenous injection; day 0 and 6)
3. Anti-AILIM antibody (1 mg/kg; intravenous injection; day 0, 3, and 6)
4. Anti-AILIM antibody (1 mg/kg; intravenous injection; day 0, 3, 6, 9, and 12)
5. Anti-AILIM antibody (0.3 mg/kg; intravenous injection; day 0, 3, 6, 9, and 12)

6. FK-506 (1 mg/kg; intramuscular injection; day 0)

7. Anti-AILIM antibody (1 mg/kg; intravenous injection; day 0) and FK-506 (1 mg/kg; intramuscular; day 0)

Duration of graft survival of the transplanted liver in the recipient was evaluated and determined according to the Kaplan-Meier test.

<2> Results

The results are shown in FIG. 1 and FIG. 2. Parts of the data in FIG. 2 are updates of the data in FIG. 1.

As a result, in the group to which the anti-AILIM antibody (1 mg/kg) was administered 3 times or 5 times over a course of time following transplantation, a significant prolongation of graft survival of the transplanted liver was observed compared to that of the control.

Furthermore, in the group to which a low dosage of anti-AILIM antibody (0.3 mg/kg) was administered 5 times over a course of time following transplantation, a similar significant prolongation of graft survival of the transplanted liver was also observed.

Furthermore, surprisingly, when the anti-AILIM antibody was administered even just once in combination with FK-506, which is an immunosuppressive agent clinically used for multiple purposes, graft survival of the transplanted liver was greatly prolonged, which was considerably longer than when only FK-506 (1 mg/kg) was administered once.

From these results, the following were revealed.

1) The anti-AILIM antibody significantly suppresses graft rejection (immunological rejection) that accompanies the transplantation of a graft such as an organ.

2) Graft rejection that accompanies the transplantation of a graft such as an organ can be further suppressed by using the anti-AILIM antibody in combination with an immunosuppressive agent, compared to when only one of them is used.

Example 2

Suppression of Immunological Rejection in Heart Transplantation by an Anti-AILIM Monoclonal Antibody <1> Reagents, Animals, and Testing Method <1-1> Animals Adult C3H/He mice (male, 6 weeks old) and BALB/c mice (male, 6 weeks old) were used as recipients and donors, respectively.

<1-2> Preparation of an Anti-Mouse AILIM Monoclonal Antibody

The preparation was done as follows.

Using the cDNA encoding the full length amino acid sequence of the previously reported mouse AILIM (Int. Immunol., Vol. 12, No. 1, p. 51-55, 2000), a transformed cell expressing mouse AILIM was prepared according to standard methods using genetic recombination technology.

The transformed cell was homogenized and ultra-centrifuged (100,000×g), and the centrifuged residue containing the cell membrane fraction was collected and suspended in PBS. The obtained cell membrane fraction was injected together with complete Freund's adjuvant into the foot pad of a Wistar rat for the initial immunization (day 0). In addition, the cell membrane fraction was administered as an antigen into the foot pad with intervals, on day 7, day 14, and day 28. Two days after the final immunization, lymph node cells were collected.

The lymph node cells and mouse myeloma cells PAI (JCR No. B0113; Res. Disclosure, Vol. 217, p. 155, 1982) were mixed in a 5:1 ratio, and a monoclonal antibody-producing hybridoma was prepared by fusing the cells using polyethylene glycol 4000 (Boehringer Mannheim) as the fusing agent. Hybridoma selection was performed by culturing in a HAT-containing ASF104 medium (Ajinomoto) containing 10% fetal bovine serum and aminopterin.

The fluorescence intensities of cells stained by reacting the culture supernatants of each hybridoma with the above-mentioned recombinant mouse AILIM-expressing transfected cells and then reacting them with FITC-labeled anti-rat IgG (Cappel) were measured using the EPICS-ELITE flow cytometer to confirm the reactivity of the monoclonal antibodies produced in the culture supernatant of each hybridoma against mouse AILIM. As a result, several hybridomas that produced monoclonal antibodies having reactivity towards mouse AILIM were obtained.

One of these hybridomas was named "B10.5". This hybridoma ($10^6$ to $10^7$ cells/0.5 mL/mouse each) was injected intraperitoneally to an ICR nu/nu mouse (female, 7 to 8 weeks old). Ten to twenty days later, laparotomy was performed on the mouse under anesthesia, and large scale preparation of rat anti-mouse AILIM monoclonal antibody (IgG2a) was carried out from the ascites obtained according to standard procedures. Hereinafter, this antibody is simply referred to as "anti-AILIM antibody".

<1-3> Heart Transplantation

Following the previously reported method, the hearts of donor BALB/c mice were transplanted to the abdomens of the recipient C3H/He mice. Disappearance of pulsation of the transplanted heart was judged to be the completion of graft rejection.

<2> Experiment 1 (Administration of Anti-AILIM Antibody)

To each C3H/He mouse (10 mice) that had completed transplantation, the anti-AILIM antibody (10 mg/kg) was administered immediately after transplantation (day 0; 200 µg), on day 2 (200 µg), day 4 (200 µg), day 7 (200 µg), and day 10 (100 µg). The group to which anti-AILIM antibody was not administered (25 mice) was used as the control.

Duration of graft survival of the transplanted heart in the recipient following transplantation was evaluated and determined according to the Kaplan-Meier test.

The average duration of graft survival of the transplanted heart in the recipients was as follows:

(Anti-AILIM Antibody Administered Group)

duration of graft survival: 9 days in 1 mouse, 10 days in 3 mice, 13 days in 4 mice, 16 days in 2 mice (Control Group)

duration of graft survival: 6 days in 2 mice, 7 days in 9 mice, 8 days in 7 mice, 9 days in 3 mice, 10 days in 4 mice The duration of graft survival in the control group to which the anti-AILIM antibody was not administered was 7.9 days, but in contrast, it was 12.3 days in the anti-AILIM antibody administered group, and a significant prolongation of graft survival of the transplanted heart was demonstrated in the anti-AILIM antibody administered group.

<3> Experiment 2 (Administration of Anti-AILIM Antibody)

The animals (donors and recipients) and the anti-AILIM antibody used were the same as those mentioned above.

Heart transplantation was carried out in a manner similar to Experiment 1.

To each C3H/He mouse that had completed the transplantation, the anti-AILIM antibody (100 μg/day) was administered intraperitoneally immediately following transplantation (day 0), on day 2, day 4, day 7, and day 10. The group to which the anti-AILIM antibody was not administered was used as the control.

The average duration of graft survival of the transplanted heart in the recipient mice was approximately 7.7 days in the control group, whereas in the anti-AILIM antibody administered group, it was approximately 40.9 days (intermediate value: 29 days/maximum value: 120 days) (FIG. 3). Namely, in the anti-AILIM antibody administered group, a significant prolongation of graft survival of the transplanted heart was demonstrated.

Furthermore, by hematoxylin/eosin-staining (HE staining) according to standard methods, the degree of infiltration of AILIM (ICOS) expressing cells into the transplanted heart was analyzed in each of the control mice (no therapeutic treatment after heart transplantation) and the mice to which anti-AILIM antibody was administered after transplantation.

As a result, in the untreated group, a significant infiltration of AILIM (ICOS) expressing cells as well as necrosis of the cardiac muscle was observed (stained portion). On the other hand, in the transplanted heart of a mouse to which anti-AILIM antibody was administered, necrosis of the cardiac muscle could not be observed, and a significant decrease of infiltration of AILIM (ICOS) expressing cells was confirmed (FIG. 4).

Example 3

Administration of AILIM-Ig to Suppress Immunological Rejection in Heart Transplantation <1> Reagents, Animals, and Testing Method <1-1> Animals Adult C3H/He mice (male, 6 weeks old) and BALB/c mice (male, 6 weeks old) are used as recipients and donors, respectively.

<1-2> Preparation of AILIM-Ig

AILIM-Ig can be a fusion protein between IgG-Fc and the extracellular region of mouse AILIM prepared similarly to a previous report (PCT Publication No. WO98/38216; European Patent Application No. EP0984023).

<1-3> Heart Transplantation

Following the previously reported method, the hearts of donor BALB/c mice are transplanted to the abdomens of the recipient C3H/He mice. Disappearance of pulsation of the transplanted heart is judged to be the completion of graft rejection.

<2> Administration of AILIM-Ig

To each C3H/He mouse that completes the transplantation, the AILIM-Ig (100 μg/day) is administered intraperitoneally immediately following transplantation (day 0), on day 2, day 4, day 7, and day 10. The group to which the AILIM-Ig is not administered is used as the control.

The duration of graft survival of the transplanted heart in the recipient mice is measured.

Example 4

Suppression of Immunological Rejections by AILIM Modulating Substances in Heart and Skin Transplantation <1> Reagents, Animals, and Testing Method <1-1> Adenovirus Vector A recombinant adenovirus containing an expression cassette of either a cDNA encoding hCTLA4-Ig (fusion protein comprising the extracellular region of human CTLA4 and human Fc) or *E. coli* β-galactosidase gene (lacZ) was produced by homologous recombination between expression cosmid cassette pAdex/CAhCTLA4-Ig (Transplantation, Vol. 68, No. 6, p. 758, 1999) and the genome of the parent strain adenovirus (Proc. Natl. Acad. Sci. USA., Vol. 90, No. 24, p. 11498-11502, 1993).

Next, the recombinant virus was proliferated within the 293 cell line derived from human kidney. The virus vector prepared in this manner was collected, and stored by freezing at −80° C. The recombinant adenovirus containing the cDNA of hCTLA4-Ig, and the adenovirus containing LacZ were named AdCTLA4-Ig and AdLacZ, respectively.

<1-2> Animals and Antibody

Adult male (210-250 g) Lewis ($RT1^l$) rats were used as recipients, and an adult male (210-250 g) DA ($RT1^a$) rats or BN ($RT1^n$) rats were used as donors.

The mouse-anti-rat AILIM monoclonal antibody prepared in Example 1 was used.

<1-3> Heart and Skin Transplantation and Method of Testing

Following a previously reported method (J. Thorac. Cardiovasc. Surg., Vol. 57, No. 2, p. 225-229, 1969), hearts obtained from DA rats were transplanted to the abdomen of Lewis rats. Immediately after the heart transplantation, an anti-rat AILIM antibody (1 mg/kg) and/or AdCTLA4-Ig ($10^9$ plaque-forming unit; pfu) were administered intravenously in a single dose to the recipient rats.

The group of transplanted animals to which neither the anti-rat AILIM antibody nor AdCTLA4-Ig was administered, and the group of transplanted animals to which AdLacZ was administered instead were used as controls. The method of treatment of each animal group is as shown below.

Group 1: Allotransplantation (Lewis/DA) without immunosuppressive treatment.

Group 2: Isotransplantation (Lewis/Lewis) without immunosuppressive treatment.

Group 3: Allotransplantation (Lewis/DA) with administration of AdLacZ.

Group 4: Allotransplantation (Lewis/DA) with administration of AdCTLA4-Ig.

Group 5: Allotransplantation (Lewis/DA) with administration of anti-AILIM antibody.

Group 6: Allotransplantation (Lewis/DA) with administration of AdCTLA4-Ig and anti-AILIM antibody.

Disappearance of pulsation of the transplanted heart was judged to be the completion of graft rejection. The graft rejection was confirmed by histologically analyzing mononuclear cells that infiltrated into the transplanted heart tissue and necrosis of the muscle cells by HE staining according to standard methods.

Next, to the lateral thoracic wall of the recipient rats of Group 4 and Group 6 in which the transplanted heart survived for a long period, a sufficiently thick skin graft of a DA donor rat was transplanted on day 140 from the heart transplantation. After the skin transplantation, an immunosuppressive treatment with the anti-AILIM antibody, AdCTLA4-Ig, or such, was not performed. The end of the duration of graft survival of the skin graft was determined when the degree of visually observable skin graft decreased to 10% or less of the initial state.

Then, on day 200 from the initial transplantation of the DA rat heart, using the cuff technique (Acta. Pathol. Microbiol. Scand. [A], Vol. 79, No. 4, p. 366-372, 1971), the heart of a donor DA rat was transplanted again to the cervical region of 3 recipient rats of Group 6 that indicated graft rejection upon receiving transplantation of donor skin.

Furthermore, on day 150 from the initial heart transplantation from DA donor rats, BN donor rat hearts were transplanted to the remaining recipient rats of Group 6 in which the transplanted heart survived for a long period.

Statistical evaluation of the survival degree of the graft in the recipients was performed according to the Kaplan-Meier test.

<2> Examination Results

As shown in FIG. 5, a significant prolongation of graft survival of the transplanted heart in recipients compared to the group of untreated animals to which xenotransplantation was performed (Group 1), was not observed in the group of AdLacZ-administered animals (Group 3) and in the group of animals to which a single dose of the anti-AILIM antibody was given (Group 5).

On the other hand, in the group of AdCTLA4-Ig-administered animals (Group 4), graft survival of the transplanted heart (initially transplanted DA rat heart) was significantly prolonged (the average: approximately 64 days). Furthermore, in 3 rats of Group 4 (10 rats), graft survival of the transplanted heart for a long period of 100 days or more was observed (FIG. 5).

Furthermore, in the group of animals in which AdCTLA4-Ig and anti-AILIM antibody were used in combination (Group 6), graft survival of the transplanted heart (initial DA rat heart) was indefinitely prolonged (300 days or more) in all recipients (FIG. 5).

In the recipient rats of Group 4, the transplanted heart (initially transplanted DA donor rat heart) was rejected along with the rejection of the transplanted skin, whereas in the recipient rats of Group 6, rejection of the transplanted heart was not observed.

As shown in FIG. 6, in all the recipient rats of Group 4 and Group 6 receiving transplantation of skin from a donor, the transplanted skin was rejected. However, in contrast to Group 4 and the control group in which rejection of the transplanted skin completed in 12 days or less from skin transplantation, the completion of rejection was somewhat delayed and was seen within 16 days or less in Group 6. This result shows that combined use of AdCTLA4-Ig and anti-AILIM antibody can delay rejection of the grafted skin compared to the case when AdCTLA4-Ig is used alone.

Interestingly, in the recipient rats of Group 6 in which long term graft survival of the transplanted heart (initial DA rat heart) was confirmed, the transplanted skin was completely rejected as mentioned above, but graft survival was seen for an indefinite period in the second transplanted heart (DA donor rat heart transplanted the second time). Furthermore, in the recipient rats, the initially transplanted donor heart survived throughout the examination.

In the recipient of Group 6 to which BN donor rat hearts were transplanted, the initially transplanted DA rat hearts continued to pulsate and survived during the examination, but the BN donor rat hearts transplanted the second time were rejected within a period similar to the results of animals of Group 1.

INDUSTRIAL APPLICABILITY

The pharmaceutical compositions of the present invention are extremely useful in the suppression, prevention, and/or treatment of immunological rejection (graft rejection), a serious problem accompanying therapies by transplantation (allotransplantation or xenotransplantation) of organs (liver, heart, lungs, kidneys, pancreas, etc.), parts thereof, or tissues (skin, cornea, bone, etc.) from donors to recipients affected by severe cardiovascular diseases.

The pharmaceutical compositions of this invention can also more strongly suppress graft rejections when used in combination with existing immunosuppressive agents that are administered to suppress graft rejections (immunological rejections) in such transplantation therapies.

Furthermore, a pharmaceutical composition comprising a human antibody against AILIM included in the pharmaceutical compositions of this invention is an extremely useful medicament, because it does not cause any side effects such as allergy when the antibody derived from mice is administered to humans.

What is claimed is:

1. A method for suppressing, treating, or preventing graft rejection accompanying the transplantation of a liver, a heart, or a portion thereof in a subject, the method comprising administering to the subject an effective amount of a pharmaceutical composition comprising (i) an antibody or a portion thereof that binds to human AILIM, and (ii) a pharmaceutically acceptable carrier.

2. A method for enhancing the effect of at least one immunosuppressive agent on the suppression, treatment, or prevention of graft rejection accompanying the transplantation of a liver, a heart, or a portion thereof in a subject, the method comprising administering to the subject at least one immunosuppressive agent and an effective amount of a pharmaceutical composition comprising (i) an antibody or a portion thereof that binds to human AILIM, and (ii) a pharmaceutically acceptable carrier.

3. A method for suppressing, treating, or preventing graft rejection accompanying the transplantation of a liver, a heart, or a portion thereof in a subject, the method comprising administering to the subject an effective amount of a pharmaceutical composition comprising (i) an antibody or a portion thereof that binds to human AILIM, and (ii) a pharmaceutically acceptable carrier, in combination with at least one immunosuppressive agent.

4. The method of claim 2, wherein the at least one immunosuppressive agent is selected from the group consisting of azathioprine, adrenocortical steroid, mizoribine, mycophenolate mofetil, leflunomide, sirolimus, deoxyspergualin, FTY720, and CTLA4 drug.

5. The method of claim 2, wherein the at least one immunosuppressive agent is cyclosporin.

6. The method of claim 2, wherein the at least one immunosuppressive agent is tacrolimus.

7. The method of claim 2, wherein the at least one immunosuppressive agent is CTLA4 drug.

8. The method of claim 1, wherein the transplantation is allotransplantation.

9. The method of claim 1, wherein the transplantation is xenotransplantation.

10. The method of claim 3, wherein the at least one immunosuppressive agent is selected from the group consisting of azathioprine, adrenocortical steroid, mizoribine, mycophenolate mofetil, leflunomide, sirolimus, deoxyspergualin, FTY720, and CTLA4 drug.

11. The method of claim 3, wherein the at least one immunosuppressive agent is cyclosporin.

12. The method of claim 3, wherein the at least one immunosuppressive agent is tacrolimus.

13. The method of claim 3, wherein the at least one immunosuppressive agent is CTLA4 drug.

14. The method of claim 2, wherein the transplantation is allotransplantation.

15. The method of claim 2, wherein the transplantation is xenotransplantation.

16. The method of claim 3, wherein the transplantation is allotransplantation.

17. The method of claim 3, wherein the transplantation is xenotransplantation.

18. The method of claim 1, wherein the antibody or portion thereof is a monoclonal antibody.

19. The method of claim 18, wherein the monoclonal antibody is a chimeric monoclonal antibody, a humanized monoclonal antibody, or a human monoclonal antibody.

20. The method of claim 1, wherein the antibody or portion thereof is an $F(ab')_2$ fragment, an Fab' fragment, an Fab fragment, an Fv fragment, or a single domain antibody.

21. The method of claim 2, wherein the antibody or portion thereof is a monoclonal antibody.

22. The method of claim 21, wherein the monoclonal antibody is a chimeric monoclonal antibody, a humanized monoclonal antibody, or a human monoclonal antibody.

23. The method of claim 2, wherein the antibody or portion thereof is an $F(ab')_2$ fragment, an Fab' fragment, an Fab fragment, an Fv fragment, or a single domain antibody.

24. The method of claim 3, wherein the antibody or portion thereof is a monoclonal antibody.

25. The method of claim 24, wherein the monoclonal antibody is a chimeric monoclonal antibody, a humanized monoclonal antibody, or a human monoclonal antibody.

26. The method of claim 3, wherein the antibody or portion thereof is an $F(ab')_2$ fragment, an Fab' fragment, an Fab fragment, an Fv fragment, or a single domain antibody.

* * * * *

UNITED STATES PATENT AND TRADEMARK OFFICE
CERTIFICATE OF CORRECTION

| | | |
|---|---|---|
| PATENT NO. | : 7,438,905 B2 | Page 1 of 1 |
| APPLICATION NO. | : 10/793171 | |
| DATED | : October 21, 2008 | |
| INVENTOR(S) | : Seiichi Suzuki, deceased et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1100 days.

Signed and Sealed this

Twenty-third Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,438,905 B2 | |
| APPLICATION NO. | : 10/793171 | |
| DATED | : October 21, 2008 | |
| INVENTOR(S) | : Suzuki et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1135 days.

Signed and Sealed this
Eleventh Day of December, 2012

David J. Kappos
*Director of the United States Patent and Trademark Office*